(12) United States Patent
Durfee et al.

(10) Patent No.: US 11,633,170 B2
(45) Date of Patent: Apr. 25, 2023

(54) SYSTEMS AND METHODS FOR ULTRASOUND PROBE NEEDLE TRACKING STATUS INDICATORS

(71) Applicant: Bard Access Systems, Inc., Salt Lake City, UT (US)

(72) Inventors: Tyler L. Durfee, Stansbury, UT (US); Kelly J. Christian, Draper, UT (US); Eddie K. Burnside, North Salt Lake, UT (US); Brian S. Tanner, Layton, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 67 days.

(21) Appl. No.: 17/013,218

(22) Filed: Sep. 4, 2020

(65) Prior Publication Data

US 2021/0059636 A1   Mar. 4, 2021

Related U.S. Application Data

(60) Provisional application No. 62/895,852, filed on Sep. 4, 2019.

(51) Int. Cl.
*A61B 8/00* (2006.01)
*A61B 8/12* (2006.01)
*A61B 8/08* (2006.01)

(52) U.S. Cl.
CPC .............. *A61B 8/12* (2013.01); *A61B 8/085* (2013.01); *A61B 8/42* (2013.01); *A61B 8/4444* (2013.01);

(Continued)

(58) Field of Classification Search
CPC .......... A61B 8/12; A61B 8/085; A61B 8/461; A61B 8/58; A61B 8/42; A61B 8/4444;
(Continued)

(56) References Cited

U.S. PATENT DOCUMENTS 5,281,199 A   1/1994   Ensminger et al.
5,423,334 A   6/1995   Jordan
(Continued)

FOREIGN PATENT DOCUMENTS

EP        810893 B1      12/1997
WO   2021/046429 A1      3/2021

OTHER PUBLICATIONS

PCT/US2020/049518 filed Sep. 4, 2020 International Search Report and Written Opinion dated Nov. 30, 2020.

*Primary Examiner* — Christopher Koharski
*Assistant Examiner* — Taylor Deutsch
(74) *Attorney, Agent, or Firm* — Rutan & Tucker LLP

(57) ABSTRACT

A guidance system for guiding insertion of a needle into a body of a patient utilizes ultrasound imaging or other suitable imaging technology. The guidance system can include an imaging device including a probe for producing an image of the internal body portion target, such as a blood vessel. The imaging device can be configured to provide at least one indication of status via sensory feedback based on a determined position of the needle, for example via a plurality of light-emitting diodes located on the device. One or more sensors can be included with the probe that can sense a magnetic field associated with the needle. The system may include a processor that can receive magnetic field data sensed by the at-least-one sensor to determine the position of the needle. The system can also include a display that depicts the determined position of the needle.

30 Claims, 12 Drawing Sheets

(52) U.S. Cl.
CPC ............... *A61B 8/461* (2013.01); *A61B 8/58* (2013.01); *A61B 2562/0223* (2013.01)

(58) Field of Classification Search
CPC .......... A61B 2562/0223; A61B 8/0841; A61B 34/20; A61B 2034/2068; A61B 2034/2063
See application file for complete search history.

(56) References Cited

U.S. PATENT DOCUMENTS

| | | | |
|---|---|---|---|
| 5,775,322 A | 7/1998 | Silverstein et al. | |
| 5,848,989 A | 12/1998 | Villani | |
| 5,879,297 A | 3/1999 | Haynor et al. | |
| 6,129,668 A | 10/2000 | Haynor et al. | |
| 6,216,028 B1 | 4/2001 | Haynor et al. | |
| 6,263,230 B1 | 7/2001 | Haynor et al. | |
| 6,565,525 B1 | 5/2003 | Burbank et al. | |
| 8,388,541 B2 | 3/2013 | Messerly et al. | |
| 8,781,555 B2 | 7/2014 | Burnside et al. | |
| 8,849,382 B2 | 9/2014 | Cox et al. | |
| 9,168,365 B2 | 10/2015 | Bourne et al. | |
| 9,456,766 B2 | 10/2016 | Cox et al. | |
| 9,492,097 B2 | 11/2016 | Wilkes et al. | |
| 9,521,961 B2 | 12/2016 | Silverstein et al. | |
| 9,554,716 B2 | 1/2017 | Burnside et al. | |
| 9,636,031 B2 | 5/2017 | Cox | |
| 9,649,048 B2 | 5/2017 | Cox et al. | |
| 9,707,339 B2 | 7/2017 | Chartrand et al. | |
| 10,449,330 B2 | 10/2019 | Newman et al. | |
| 10,524,694 B2 | 1/2020 | Hunter | |
| 10,751,509 B2 | 8/2020 | Misener | |
| 2004/0267121 A1 | 12/2004 | Sarvazyan et al. | |
| 2010/0298705 A1 | 11/2010 | Pelissier et al. | |
| 2012/0143029 A1 | 6/2012 | Silverstein et al. | |
| 2013/0218024 A1 | 8/2013 | Boctor et al. | |
| 2013/0303896 A1 | 11/2013 | Kalpin et al. | |
| 2014/0023999 A1* | 1/2014 | Greder | A61B 5/375 434/236 |
| 2014/0243789 A1 | 8/2014 | Mehta et al. | |
| 2015/0196704 A1 | 7/2015 | Adler | |
| 2016/0067470 A1 | 3/2016 | Silva Pires e Albuquerque | |
| 2016/0278869 A1* | 9/2016 | Grunwald | A61B 8/4472 |
| 2017/0281086 A1* | 10/2017 | Donaldson | A61B 5/14542 |
| 2018/0310955 A1 | 11/2018 | Lindekugel et al. | |
| 2019/0053858 A1 | 2/2019 | Kapoor et al. | |
| 2019/0125470 A1 | 5/2019 | Moskowitz et al. | |
| 2019/0232035 A1 | 8/2019 | Fedor et al. | |

\* cited by examiner

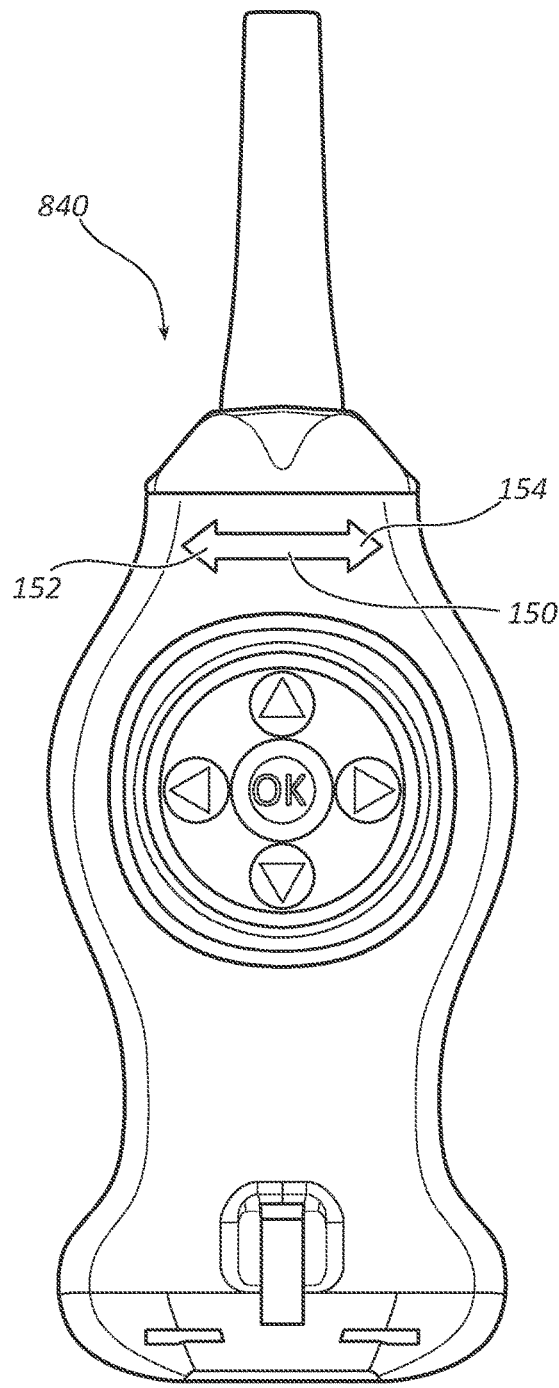
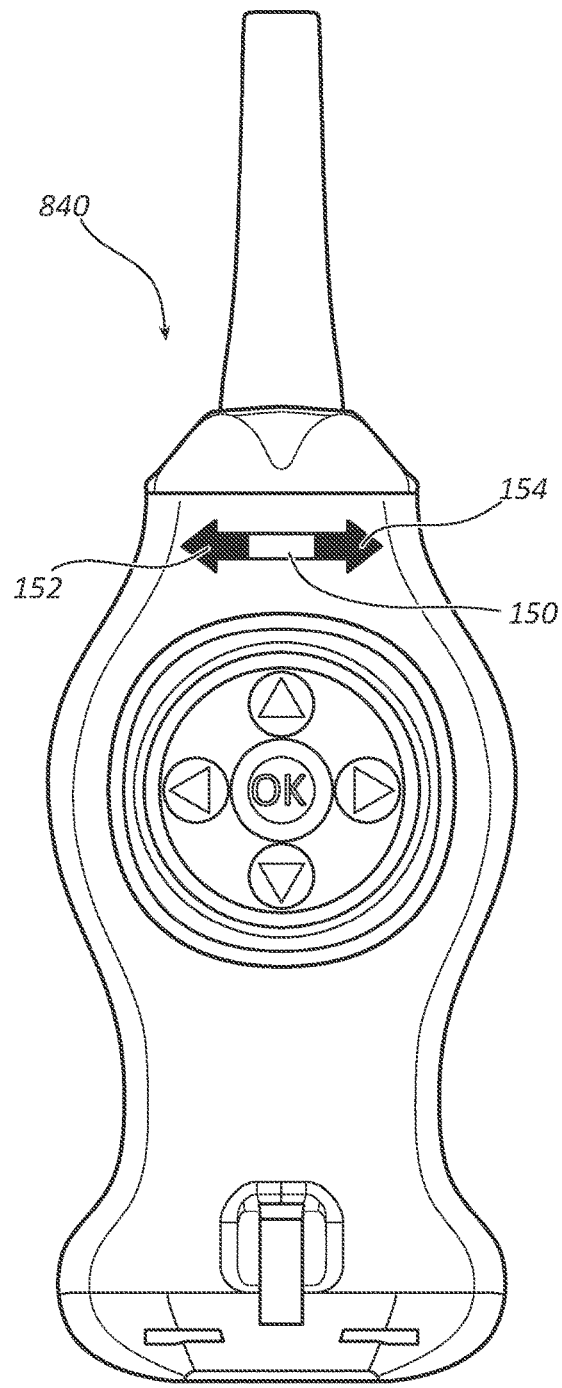
FIG. 8A                    FIG. 8B

SYSTEMS AND METHODS FOR ULTRASOUND PROBE NEEDLE TRACKING STATUS INDICATORS

PRIORITY

This application claims the benefit of priority to U.S. Provisional Application No. 62/895,852, filed Sep. 4, 2019, which is incorporated by reference in its entirety into this application.

BACKGROUND

Medical device tracking and guidance is described for various instruments, such as catheters, stylets, and needles, among the following U.S. patents, each of which is incorporated by reference in its entirety into this application: U.S. Pat. Nos. 9,649,048; 9,636,031; 9,554,716; 9,521,961; 9,492,097; 9,456,766; 8,849,382; 8,781,555; 8,388,541; 10,751,509; 10,449,330; and 10,524,694. However, there is an ongoing need to improve guidance for medical devices including at the human interfaces between guidance systems and the medical devices guided thereby.

Disclosed herein are guidance systems, medical devices, and methods that address the foregoing need to improve guidance for medical devices.

SUMMARY

Briefly summarized, embodiments described herein are directed to an integrated catheter placement system and a method for accurately placing a catheter within the vasculature of a patient via a series of integrated status indication systems and methods. The integrated system can employ, for example, at least three modalities for improving catheter placement accuracy: 1) ultrasound-assisted guidance for introducing the catheter into the patient's vasculature; 2) a tip location system ("TLS"), or magnetically-based (e.g., via permanent magnet(s) or electromagnet(s)) tracking of the catheter tip during its advancement through the vasculature to detect and facilitate correction of any tip malposition during such advancement; and 3) status indicators that allow a clinician to improve the tracking and guidance of a needle by providing information relating to calibration and/or suggested directions for movement based on the tracking.

In one embodiment, the guidance system for guiding insertion of a needle into a body of a patient comprises an ultrasound imaging device including a probe for ultrasonically imaging an internal body portion target. At least one sensor included with the probe senses a magnetic field associated with the needle, and a processor that receives magnetic field data sensed by the sensors determines a position of the needle in three spatial dimensions. A display further depicts the determined position of the needle together with the image of the target, and the ultrasound imaging device is also configured to provide at least one indication of status via sensory feedback based on the determined position.

In other embodiments, the sensory feedback is delivered via visible light. This can include visible light produced via a plurality of light-emitting diodes located on the probe or monitor. The light-emitting diodes can be configured to emit a first series of light patterns to indicate at least one status associated with calibration of a component of the guidance system and/or a second series of light patterns to indicate a suggested direction to move the probe to increase tracking accuracy.

In additional embodiments, the light patterns can include utilizing colors to indicate the status of the system, including the suggested direction to move the needle and/or probe. Specifically, in certain embodiments, changing between at least two colors is associated with the suggested direction of movement.

Further, embodiments may contain at least two light-emitting diodes are positioned on opposing sides of the probe, and the changing between at least two of the plurality of colors of the second series of light patterns is associated with the suggested direction. These light-emitting diodes may be shaped in various ways including bi-directional and tri-directional arrows. Thus, changes in light color or intensity can create varying levels of status indication.

In many embodiments, the sensory feedback is delivered via a visual indicator on the display. This can often be accomplished via the display. Specifically, the display can be configured to emit a first color pattern to indicate at least one status associated with calibration of a component of the guidance system, a second color pattern to indicate at least one error within the guidance system and/or a third color pattern to indicate a ready or fault state within the guidance system.

Certain embodiments may be able to provide the sensory feedback through a wearable device. The wearable device can deliver visual sensory feedback (e.g., visual image) through a smart-glasses system. Other wearables may provide tactile feedback such as a vibration sensor located in a smart watch or other suitable physical contacting device that is in communication with the guidance system. In further embodiments, the sensory feedback can be provided via tactile vibrations generated within the probe.

In one embodiment, the sensory feedback is provided by audio signals generated to be heard by a clinician. The audio can be generated with multiple sounds to indicate multiple statuses within the display and/or the probe.

In another embodiment, the guidance system for guiding insertion of a needle into a body of a patient comprises an ultrasound imaging device including a probe for ultrasonically imaging an internal body portion target within a calibration zone determined by a calibration process. At least one sensor included with the probe senses a magnetic field associated with the needle, and a processor that receives magnetic field data sensed by the sensors determines a position of the needle in three spatial dimensions within the calibration zone. A display further depicts the determined position of the needle together with the image of the target, and the ultrasound imaging device is also configured to provide at least one indication of status via sensory feedback from a plurality of light-emitting diodes placed on the probe. The sensory feedback includes generating visual notifications that the probe is being moved near a border of the calibration zone.

In one embodiment, the method is for guiding a needle for insertion into a body of a patient utilizing imaging technology. The method includes (a) imaging a target within the body; (b) sensing a detectable characteristic relating to the needle via a probe; (c) determining a position of the needle in at least two spatial dimensions by data relating to the sensed detectable characteristic and the sensed extent of bending; (d) displaying the position of the needle with respect to the target together with the image of the target; and (e) providing at least one indication of status via sensory feedback based on the determined position.

In some embodiments, the sensory feedback is delivered via visible light.

In some embodiments, the visible light is produced via a plurality of light-emitting diodes located on the probe.

In some embodiments, the plurality of light-emitting diodes are configured to emit a first series of light patterns to indicate at least one status associated with calibration of a component of the guidance system.

In some embodiments, the plurality of light-emitting diodes are configured to emit a second series of light patterns to indicate a suggested direction to move the probe to increase tracking accuracy.

In some embodiments, the second series of light patterns includes utilizing a plurality of colors to indicate the suggested direction.

In some embodiments, changing between at least two colors of the plurality of colors is associated with the suggested direction.

In some embodiments, at least two light-emitting diodes of the plurality of light-emitting diodes are positioned on opposing sides of the probe. Also, changing between the at-least-two colors of the plurality of colors of the second series of light patterns is associated with the suggested direction.

In some embodiments, the sensory feedback is delivered via a visual indicator on a display.

In some embodiments, displaying further emits a first color pattern to indicate at least one status associated with the calibration status of at least one component.

In some embodiments, displaying further emits a second color pattern to indicate at least one error.

In some embodiments, displaying further emits a third color pattern to indicate a ready state.

In some embodiments, the sensory feedback is delivered via a visual image generated by a wearable device.

In some embodiments, the sensory feedback is delivered via tactile feedback generated within the probe.

In some embodiments, the providing sensory feedback further includes delivering an audio signal via a speaker.

These and other features of embodiments of the present invention will become more fully apparent from the following description and appended claims, or may be learned by the practice of embodiments of the invention as set forth hereinafter.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 8A shows a possible configuration for light-emitting diodes located on the front side of a probe of the guidance system, arranged on opposing ends and shaped in a bi-directional arrow according to one embodiment;

FIG. 8B shows the light-emitting diodes of FIG. 8A in an "on" state;

Figure 9A:
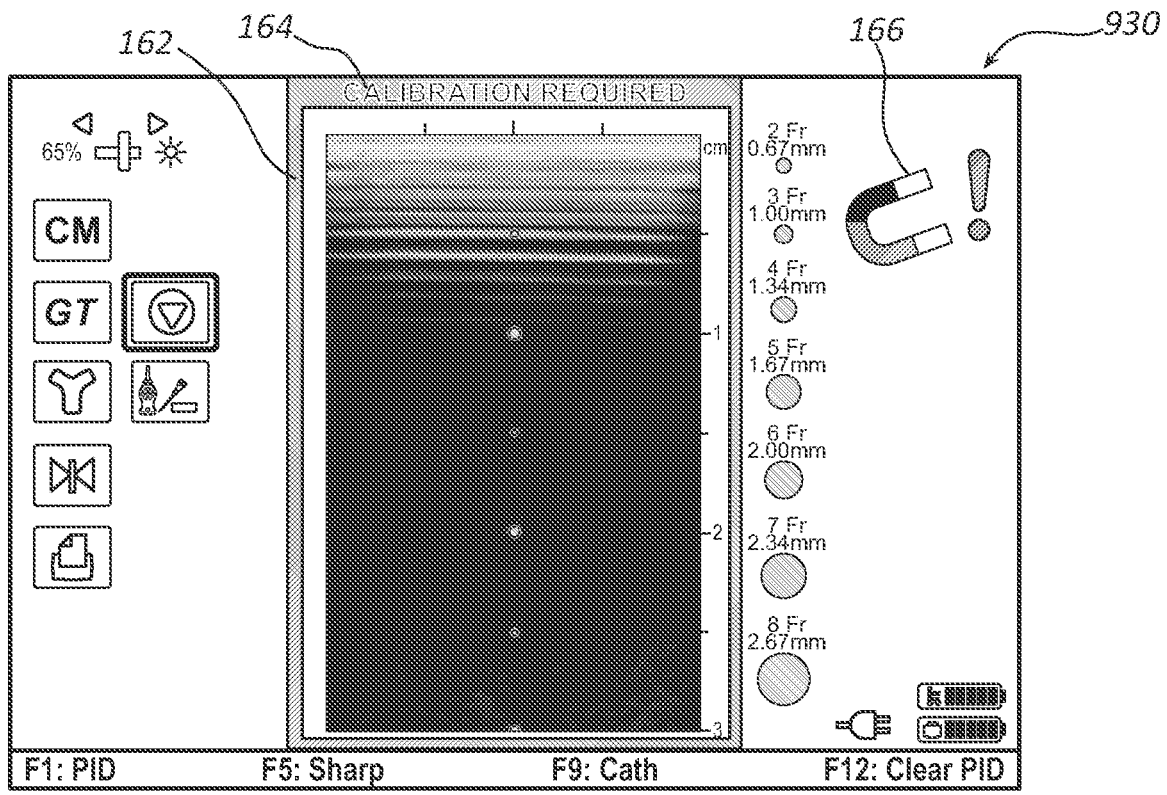
FIG. 9A shows a possible screenshot for depiction on the display of the guidance system, showing the colored status indicator border around the ultrasound viewing area, and associated icons according to one embodiment.
Figure 9B:
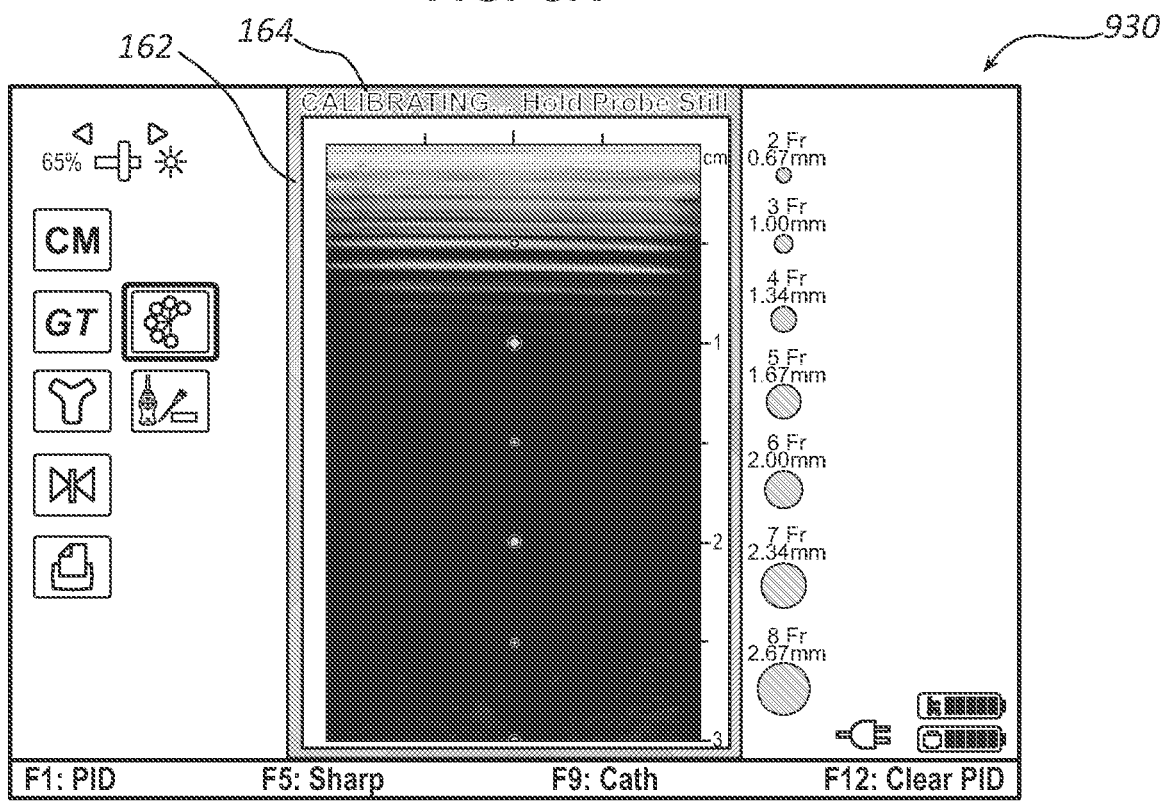
FIG. 9B shows another possible screenshot for depiction on the display of the guidance system, showing the colored status indicator border around the ultrasound viewing area, and the associated icons according to one embodiment.
Figure 9C:
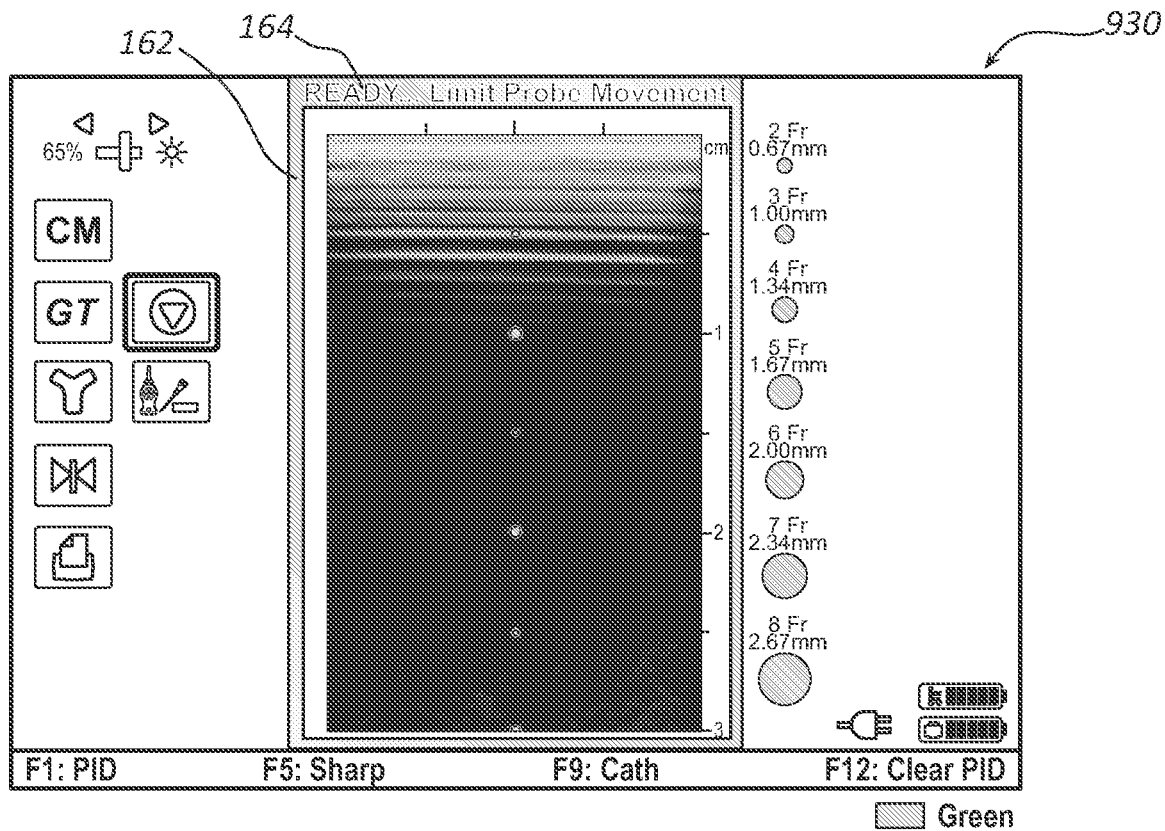
Figure 9D:
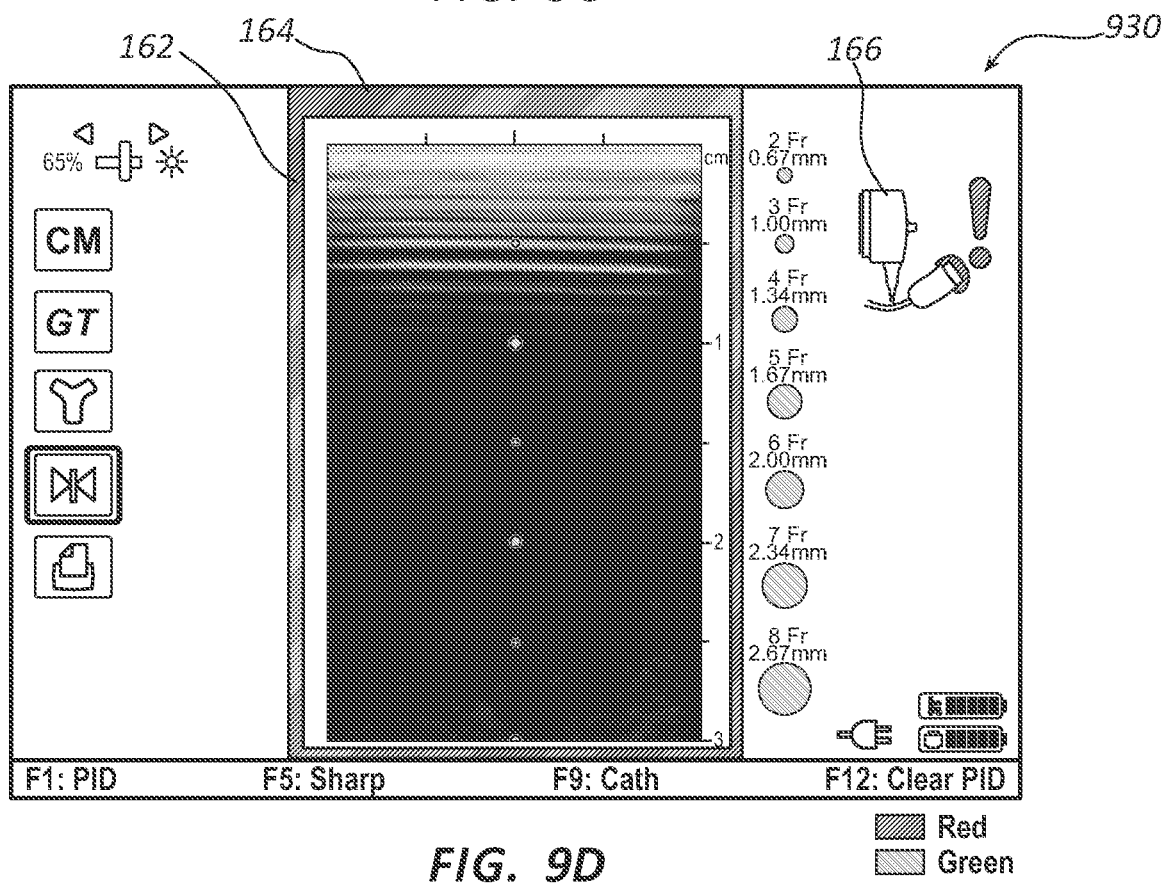

FIG. 9C shows yet another possible screenshot for depiction on the display of the guidance system, showing the colored status indicator border around the ultrasound viewing area, and the associated icons according to one embodiment; and FIG. 9D shows yet another possible screenshot for depiction on the display of the guidance system, showing the colored status indicator border around the ultrasound viewing area, and the associated icons according to one embodiment.

DESCRIPTION

Before some particular embodiments are disclosed in greater detail, it should be understood that the particular embodiments disclosed herein do not limit the scope of the concepts provided herein. It should also be understood that a particular embodiment disclosed herein could have features that can be readily separated from the particular embodiment and optionally combined with or substituted for features of any of a number of other embodiments disclosed herein.

Reference will now be made to figures wherein like structures will be provided with like reference designations. It is understood that the drawings are diagrammatic and schematic representations of exemplary embodiments of the present invention, and are neither limiting nor necessarily drawn to scale.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

As set forth above, there is an ongoing need to improve guidance for medical devices including at the human interfaces between guidance systems and the medical devices guided thereby. Disclosed herein are guidance systems, medical devices, and methods that address the foregoing need to improve guidance for medical devices.

Embodiments of the present invention described herein are generally directed to status indicators for a guidance system configured for locating and guiding a needle or other medical component during ultrasound-based or other suitable procedures for accessing with the needle a subcutaneous vessel of a patient, for instance. In many embodiments, the status indicators facilitate the user of a guidance system to enable the position, orientation, and advancement of the needle in real-time, thus better enabling a clinician to accurately guide the needle to the intended target. In some embodiments, the guidance system can track the needle's position in five degrees of motion: x, y, and z spatial coordinate space, needle pitch, and needle yaw. Certain status indicators can be configured to notify the user of the guidance system how to better orient the needle's position within these degrees of motion. Such tracking and feedback systems can enable the needle to be guided and placed with a relatively higher accuracy than guidance systems without such status indicators.

Figure 1:
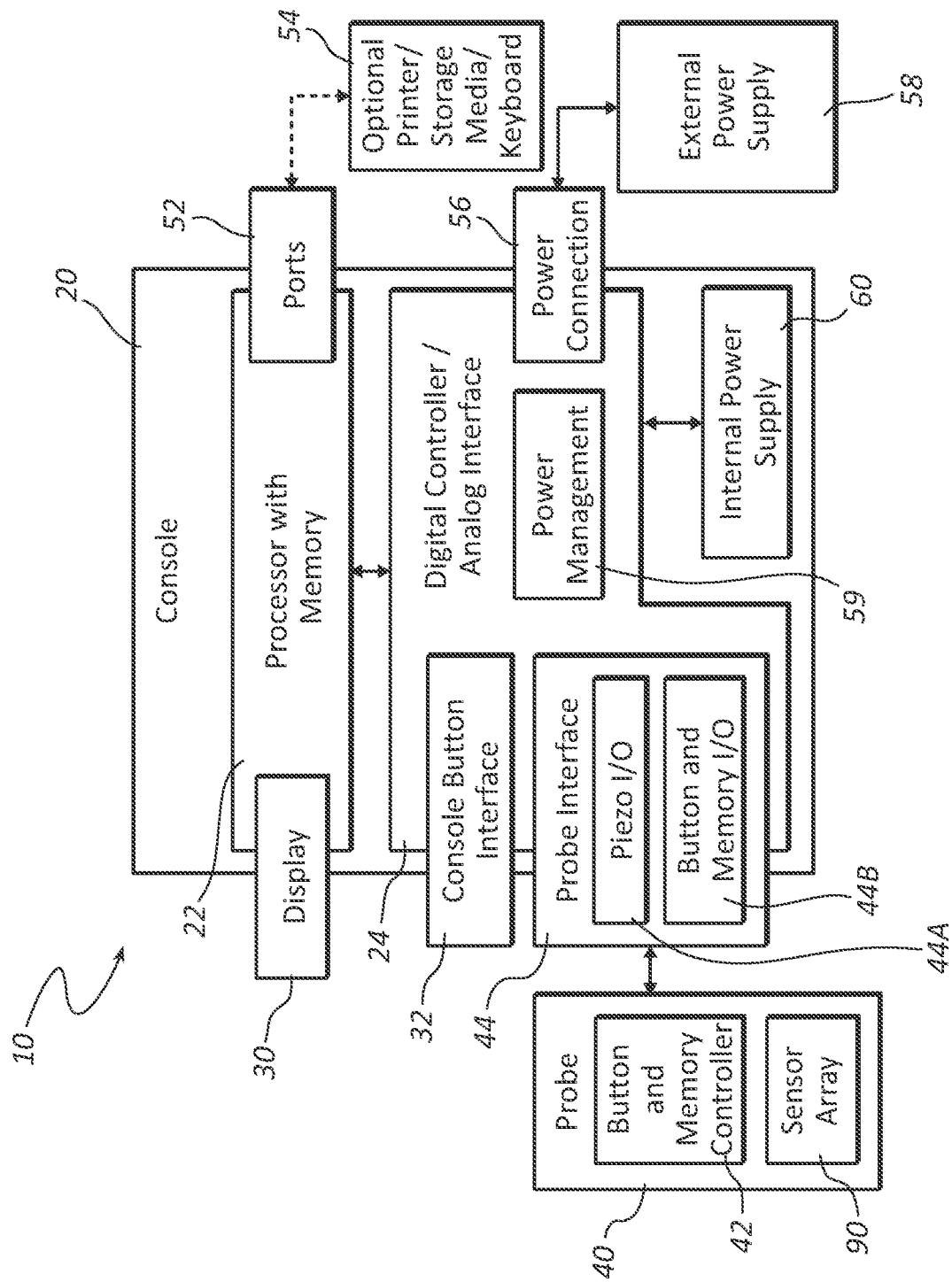
FIG. 1 is a block diagram depicting various elements of an ultrasound-based guidance system for needles and other medical components, according to one example embodiment of the present invention.
Figure 2:
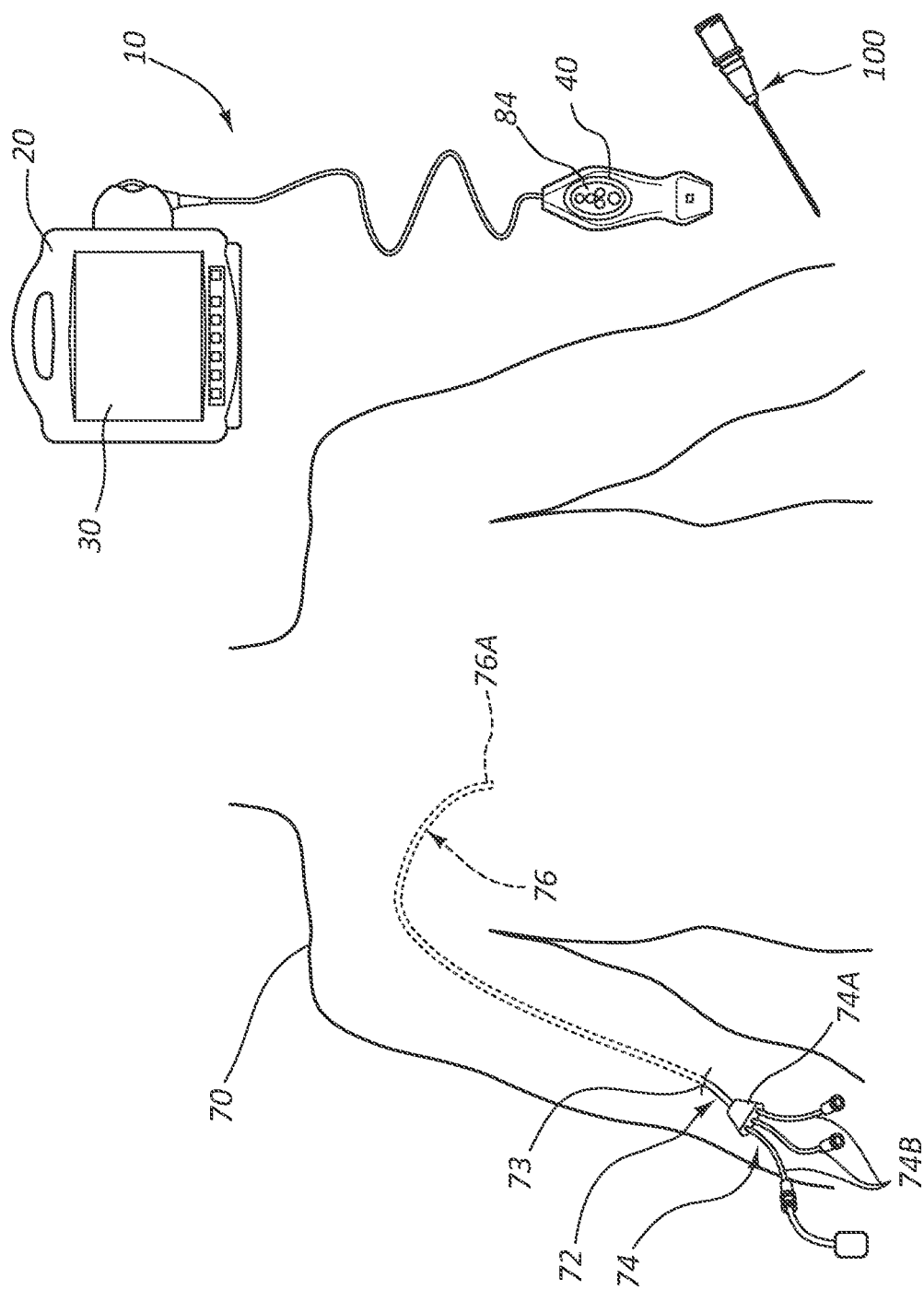
FIG. 2 is a simplified view of a patient and a catheter being inserted therein, showing one possible environment in which the guidance system of FIG. 1 can be practiced.

Reference is first made to FIGS. 1 and 2, which depict various components of an ultrasound-based needle guidance system ("system"), generally designated at 10, configured in accordance with one embodiment of the present invention. As shown, the guidance system 10 generally includes an ultrasound ("US") imaging portion including a console 20, a display 30, and a handheld ultrasound probe 40, each of which is described in further detail below. Note that the ultrasound imaging portion can be configured in one of a variety of ways in addition to what is shown and described herein.

It can be appreciated that the console 20 can take one of a variety of forms. A processor 22, including non-volatile memory such as EEPROM for instance, is included in the console 20 for controlling system function during operation of the guidance system 10, thus acting as a control processor. A digital controller/analog interface 24 is also included with the console 20 and is in communication with both the processor 22 and other system components to govern interfacing between the ultrasound probe 40 and other system components.

The guidance system 10 can further include a plurality of ports 52 for connection with optional components 54 including a printer, storage media, keyboard, etc. The ports in one embodiment are USB ports, though other port types or a combination of port types can be used for this and the other interfaces connections described herein. In certain embodiments, the ports 52 may be implemented via a wireless connection over a network. A power connection 56 is included with the console 20 to enable operable connection to an external power supply 58. An internal power supply 60 (e.g., a battery) can also be employed, either with or exclusive of an external power supply. Power management circuitry 59 is included with the digital controller/analog interface 24 of the console to regulate power use and distribution.

The display 30 in the present embodiment is a single display integrated into the console 20 and is used to display information to the clinician during a procedure. In another embodiment, the display may be separate from the console. As will be seen, the content depicted by the display 30 can change according to, for example, which mode the system is in such as, but not limited to, US, TLS, or in other embodiments, ECG tip confirmation. In certain embodiments, a console button interface 32 and buttons included on the ultrasound probe 40 can be used to immediately call up a desired mode to the display 30 by the clinician to assist in the procedure. In additional embodiments, information from multiple modes, such as TLS and ECG, may be displayed simultaneously. Thus, the display 30 of the console 20 can be employed for ultrasound guidance in accessing a patient's vasculature, TLS guidance during catheter advancement through the vasculature, and (as in later embodiments) ECG-based confirmation of catheter distal tip placement with respect to a node of the patient's heart. In further embodiments, the ultrasound probe 40 can include a plurality of control buttons 84 (see FIG. 2) which can be used to immediately call up a desired mode to the display 30 by the clinician to assist in the placement procedure. In many embodiments, the display 30 utilizes an LCD panel.

The ultrasound probe 40 can be employed in connection with a modality mentioned above, i.e., ultrasound ("US")-based visualization of a vessel, such as a vein, in preparation for insertion of a catheter 72 into the vasculature (see FIG. 2). Such visualization can give real time ultrasound guidance for introducing the catheter 72 into the vasculature of a patient 70 and can assist in reducing complications typically associated with such introductions, including inadvertent arterial puncture, hematoma, pneumothorax, etc.

FIG. 1 further shows that the ultrasound probe 40 can further include a button and memory controller 42 for governing button and probe operation. The button and memory controller 42 can include non-volatile memory, such as EEPROM, in certain embodiments. The button and memory controller 42 is in operable communication with a probe interface 44 of the console 20, which often includes a piezo input/output component 44A for interfacing with the probe piezoelectric array and a button and memory input/output component 44B for interfacing with the button and memory controller 42.

The ultrasound imaging portion of the guidance system 10 can also be employed to image a targeted internal portion of a body of a patient prior to percutaneous insertion of a needle or other device to access the target. As described below, in some embodiments, insertion of the needle is performed prior to the subsequent insertion of a catheter into a vein or other portion of the vasculature of the patient. It is appreciated, however, that insertion of a needle into the body of a patient can be performed for a variety of medical purposes.

FIG. 2 shows the general relation of the above-described components to the patient 70 during a procedure to ultimately place the catheter 72 into the patient vasculature through skin at an insertion site 73, according to one embodiment. FIG. 2 shows that the catheter 72 generally includes a proximal portion 74 that remains exterior to the patient and a distal portion 76 that resides within the patient vasculature after placement is complete. The guidance system 10 is employed to ultimately position a distal tip 76A of the catheter 72 in a desired position within the patient vasculature. In one embodiment, the desired position for the distal tip 76A of the catheter 72 is proximate the patient's heart, such as in the lower one-third ($\frac{1}{3}^{rd}$) portion of the Superior Vena Cava ("SVC"). Of course, the guidance system 10 can be employed to place the catheter distal tip in other locations.

The proximal portion 74 of the catheter 72 further includes a hub 74A that provides fluid communication between the one or more lumens of the catheter 72 and one or more extension legs 74B extending proximally from the hub. As mentioned, placement of a needle 100 into the patient vasculature at the insertion site 73 is typically performed prior to insertion of the catheter, though it is appreciated that other placement methods can be employed. Further, it is appreciated that the above discussion is only one example for use of the guidance system 10; indeed it can be employed for a variety of uses, such as the placement of needles preparatory to insertion of a catheter as above, the insertion of the needle 100 for other uses, or for the insertion of other medical components into the body of a patient, including x-ray or ultrasound markers, biopsy sheaths, ablation components, bladder scanning components, vena cava filters, etc.

In greater detail, the console 20 houses a variety of components of the guidance system 10 and it is appreciated that the console can take one of a variety of forms. The processor 22, including non-volatile memory such as EEPROM for instance, is included in the console 20 for controlling system function and executing various algorithms during operation of the guidance system 10, thus acting as a control processor. The digital controller/analog interface 24 is also included with the console 20 and is in communication with both the processor 22 and other system components to govern interfacing between the ultrasound probe 40 and other system components.

FIG. 2 further depicts the needle 100 used to gain initial access to the patient vasculature via the insertion site 73. As will be described in further detail below, the needle 100 is configured to cooperate with the guidance system 10 in enabling the system to detect the position, orientation, and advancement of the needle during an ultrasound-based placement procedure.

Figure 3:
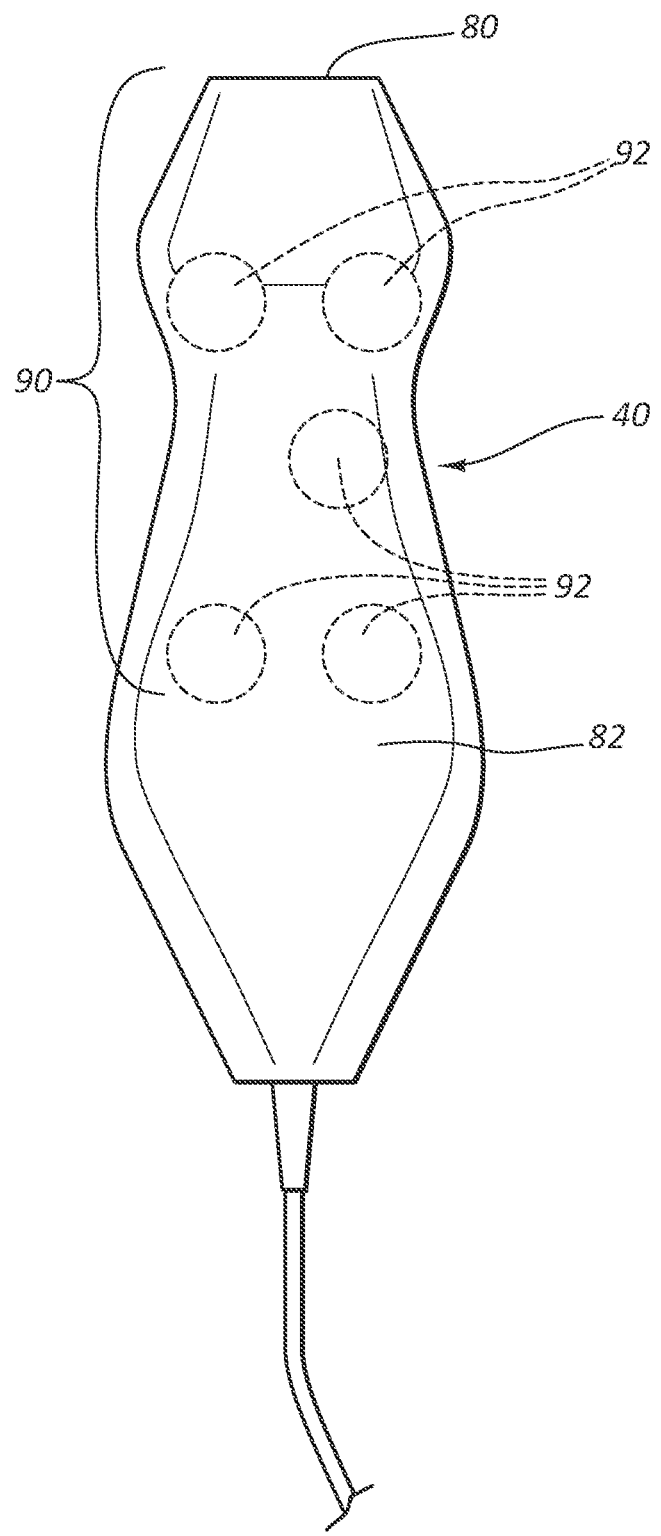
FIG. 3 is a top view of the ultrasound probe of the guidance system of FIG. 1.

FIG. 3 depicts features of the ultrasound probe 40 according to a variety of embodiments. The ultrasound probe 40 is employed in connection with ultrasound-based visualization of a vessel, such as a vein, in preparation for insertion of the needle 100 and/or the catheter 72 into the vasculature. Such visualization can give real time ultrasound guidance and assists in reducing complications typically associated with such introduction, including inadvertent arterial puncture, hematoma, pneumothorax, etc.

The ultrasound probe 40 is often configured to include a head 80 that houses a piezoelectric (or similar functioning) array for producing ultrasonic pulses and for receiving echoes thereof after reflection by the patient's body when the head is placed against the patient's skin proximate the prospective insertion site 73 (FIG. 2). The ultrasound probe 40 further includes the control buttons 84 (FIG. 2) for controlling the system, thus eliminating the need for the clinician to reach out of the sterile field, which is established about the patient insertion site prior to establishment of the insertion site, to control the guidance system 10.

As such, in one embodiment a clinician employs the ultrasound imaging portion of the guidance system 10 to determine a suitable insertion site and establish vascular access, such as with the needle 100, prior to introduction of the catheter 72 for ultimate advancement thereof through the vasculature toward an intended destination.

As seen in FIG. 3, the ultrasound probe 40 can include a sensor array 90 for detecting the position, orientation, and movement of the needle 100 during ultrasound imaging procedures, such as those described above. As will be described in further detail below, the sensor array includes a plurality of magnetic sensors 92 embedded within the housing of the probe. The magnetic sensors 92 are configured to detect a magnetic field associated with the needle 100 and enable the guidance system 10 to track the needle. Though configured here as magnetic sensors, it is appreciated that the magnetic sensors 92 can be sensors of other types and configurations, as will be described. In addition, though they are shown in FIG. 3 as included with the ultrasound probe 40, the magnetic sensors 92 of the sensor array 90 can be included in a component separate from the probe, such as a separate handheld device. Such devices can be utilized, for example, to retrofit other probes in similar devices without the magnetic sensors 92. In the present embodiment, the magnetic sensors 92 are disposed in a planar configuration below a top face 82 of the ultrasound probe 40, though it is appreciated that the sensors can be arranged in other configurations, such as in an arched or semi-circular arrangement.

In the illustrated embodiment of FIG. 3, each of the magnetic sensors 92 include three orthogonal sensor coils for enabling detection of a magnetic field in three spatial dimensions. Such three-dimensional ("3-D") magnetic sensors can be purchased, for example, from Honeywell Sensing and Control of Morristown, N.J. Further, the magnetic sensors 92 of the present embodiment are configured as Hall-effect sensors, though other types of magnetic sensors could be employed. Further, instead of 3-D sensors, a plurality of one-dimensional magnetic sensors can be included and arranged as desired to achieve 1-, 2-, or 3-D detection capability.

In the present embodiment, the magnetic sensors 92 include five magnetic sensors in the sensor array 90 so as to enable detection of the needle 100 in not only the three spatial dimensions (i.e., X, Y, Z coordinate space), but also the pitch and yaw orientation of the needle itself. Note that in one embodiment, orthogonal sensing components of two or more of the magnetic sensors 92 can enable the pitch and yaw attitude of the magnetic element 110, and thus the needle 100, to be determined.

In other embodiments, fewer or more sensors can be employed in the sensor array, depending on the application. More generally, it is appreciated that the number, size, type, and placement of the sensors of the sensor array can vary from what is explicitly shown here.

Figure 4A:
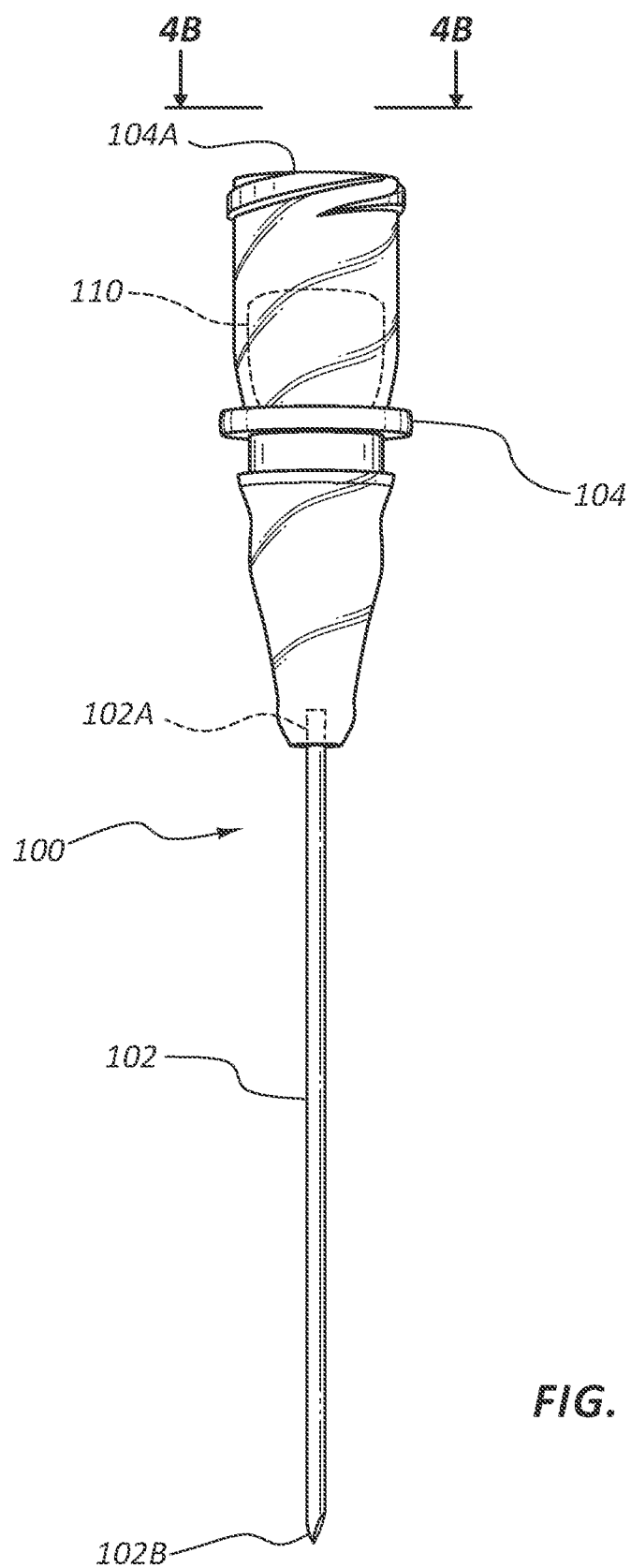
FIG. 4A is a side view of a needle for use with the guidance system of FIG. 1, according to one embodiment.
Figure 4B:
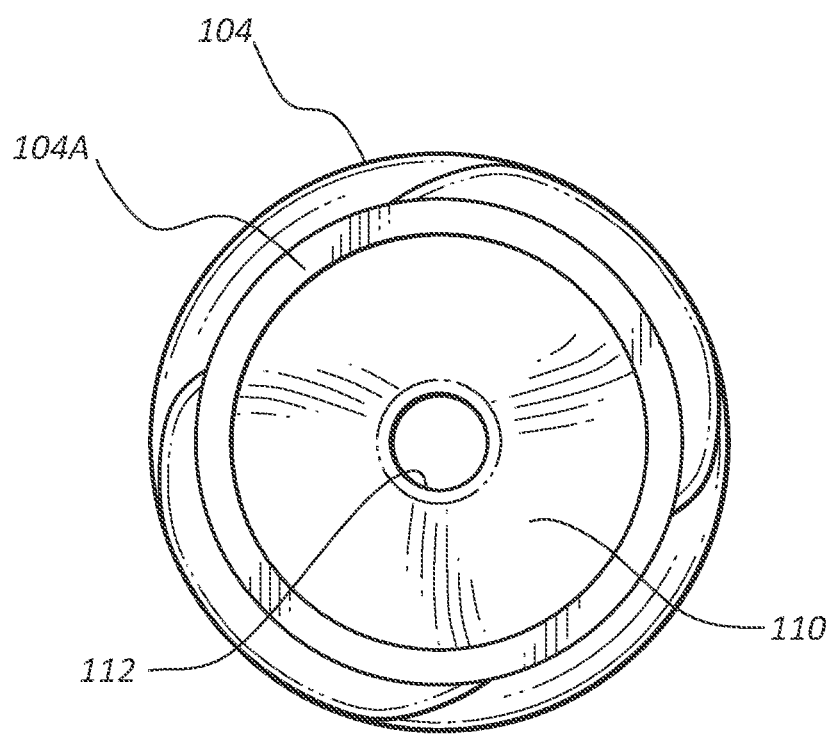
FIG. 4B is an end view of the needle of FIG. 4A.

FIGS. 4A and 4B show details of one example of the needle 100 that can be used in connection with the guidance system 10 in accessing a targeted internal body portion of the patient, as shown in FIG. 2, according to one embodiment. In particular, the needle 100 includes a hollow cannula 102, which has a proximal end 102A and a distal end 102B. A hub 104 is attached to the proximal end 102A of the cannula 102 and includes an open end 104A that is configured as a connector for connecting with various devices, in the present embodiment. Indeed, the open end 104A of the hub 104 is in fluid communication with a lumen of the cannula 102 such that a guide wire, stylet, or other component may be passed through the hub into the cannula.

As shown in FIGS. 4A and 4B, the magnetic element 110 is included with the hub 104. As best seen in FIG. 4B, the magnetic element 110 in the present embodiment is a permanent magnet, including a ferromagnetic substance for instance, and is ring-shaped so as to define hole 112 that is aligned with the cannula 102. So configured, the magnetic element 110 produces a magnetic field that is detectable by the sensor array 90 of the ultrasound probe 40 so as to enable the location, orientation, and movement of the needle 100 to be tracked by the guidance system 10, as described further below.

In other embodiments, it is appreciated that many other types, numbers, and sizes of magnetic elements can be employed with the needle 100 or other medical component to enable tracking thereof by the present guidance system.

Figure 5A:
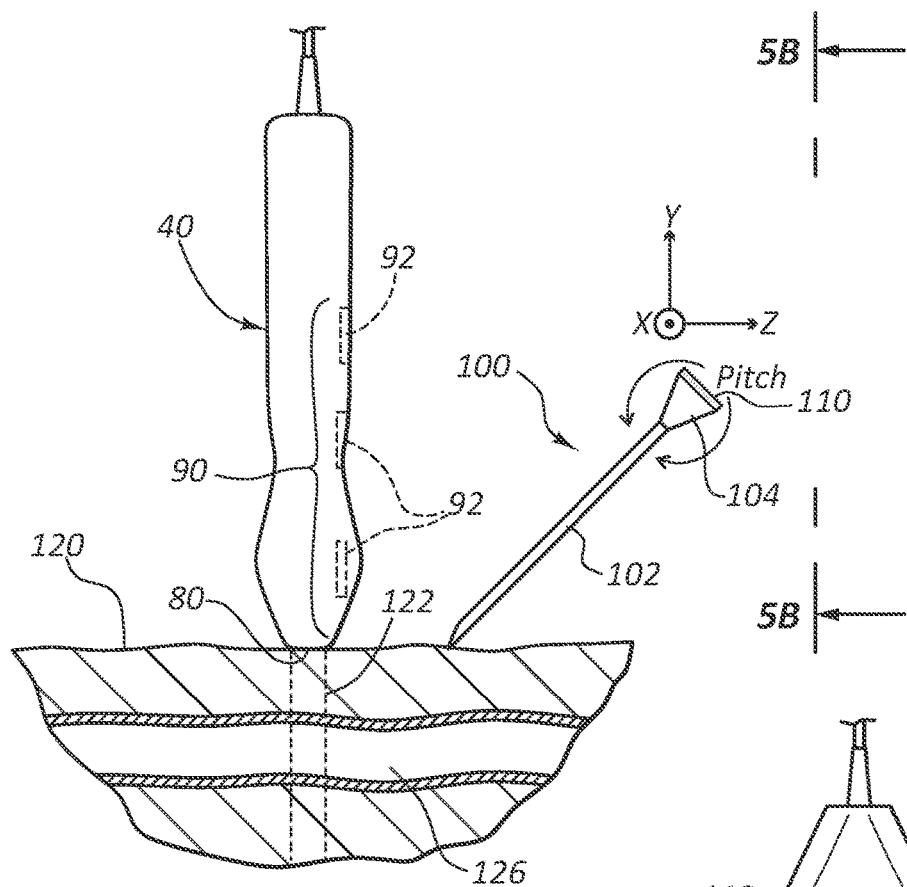
FIG. 5A is simplified view of the ultrasound probe of the guidance system being used to guide a needle toward a vessel within the body of a patient
Figure 5B:
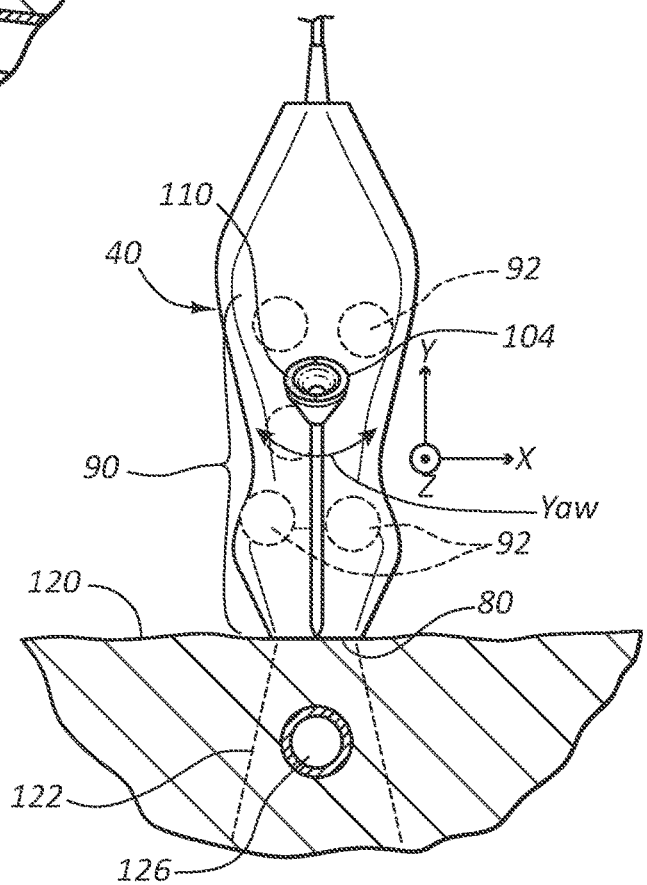
FIG. 5B is another simplified view of the ultrasound probe of the guidance system being used to guide the needle toward the vessel within the body of the patient.

Reference is now made to FIGS. 5A and 5B, which show the ultrasound probe 40 of the guidance system 10 and the needle 100 in position and ready for insertion thereof through a skin surface 120 of a patient to access a targeted internal body portion. In particular, the ultrasound probe 40 is shown with the head 80 placed against the patient skin and producing an ultrasound beam 122 so as to ultrasonically image a portion of a subcutaneous vessel 126 beneath the skin surface 120 of the patient. The ultrasonic image of the vessel 126 can be depicted on the display 30 of the guidance system 10 (FIG. 2).

As mentioned above, the guidance system 10 in the present embodiment is configured to detect the position, orientation, and movement of the needle 100 described above. In particular, the sensor array 90 of the ultrasound probe 40 is configured to detect a magnetic field associated with the magnetic element 110 included with the needle 100. Each of the magnetic sensors 92 of the sensor array 90 is configured to spatially detect the magnetic element 110 in three-dimensional space. Thus during operation of the guidance system 10, magnetic field strength data of the needle's associated magnetic element 110 sensed by each of the magnetic sensors 92 is forwarded to a processor, such as the processor 22 of the console 20 (FIG. 1), which computes in real-time the position and/or orientation of the magnetic element 110. In certain embodiments, the needle may be made of magnetic material such that the magnetic element 110 is not required for detection by the sensor array 90 of the ultrasound probe 40.

Specifically, and as shown in FIGS. 5A and 5B, the position of the magnetic element 110 in X, Y, and Z coordinate space with respect to the sensor array 90 can be determined by the guidance system 10 using the magnetic field strength data sensed by the magnetic sensors 92. Moreover, FIG. 5A shows that the pitch of the magnetic element 110 can also be determined, while FIG. 5B shows that the yaw of the magnetic element can be determined. Suitable circuitry of the ultrasound probe 40, the console 20, or other component of the system can provide the calculations necessary for such position/orientation. In one embodiment, the magnetic element 110 can be tracked using the teachings of one or more of: U.S. Pat. Nos. 5,775,322; 5,879,297; 6,129,668; 6,216,028; and 6,263,230, each of which is incorporated herein by reference in its entirety.

Figure 6A:
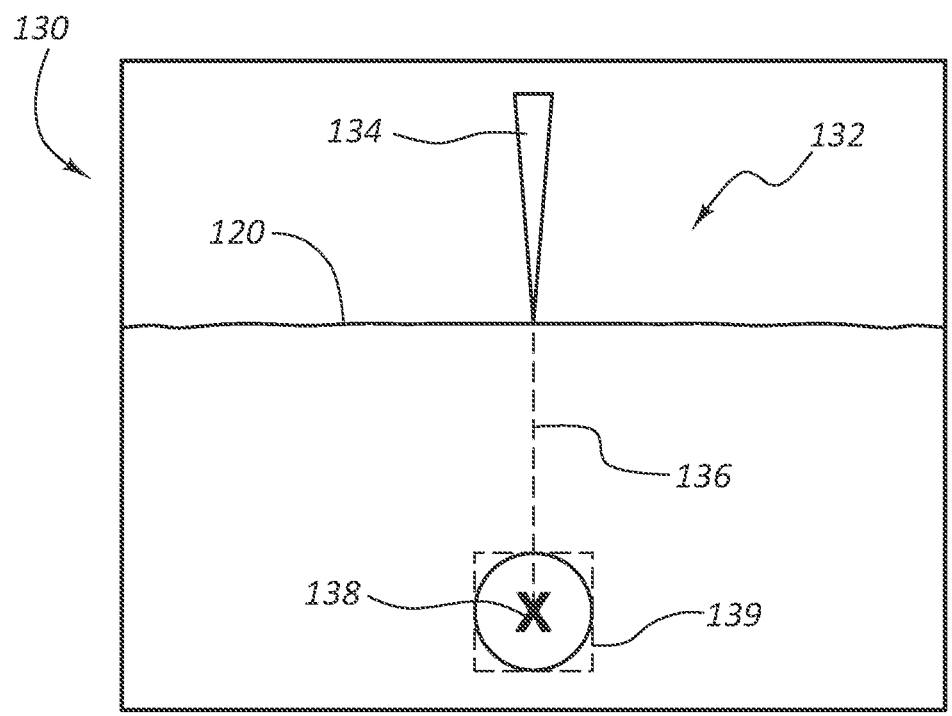
FIG. 6A shows a possible screenshot for depiction on the display of the guidance system, showing the position and orientation of a needle according to one embodiment.
Figure 6B:
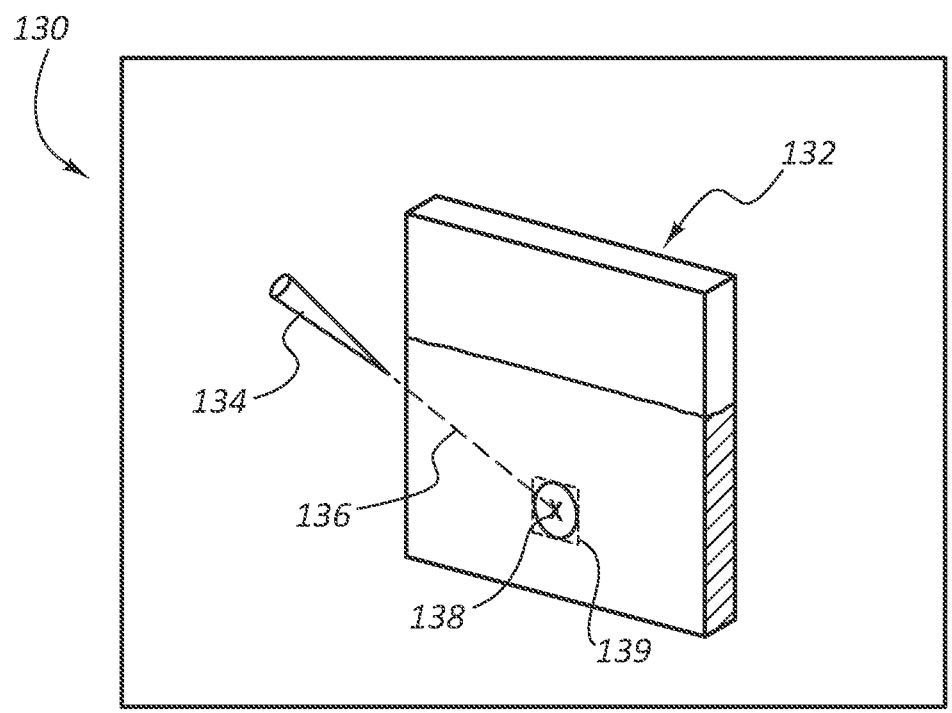
FIG. 6B shows another possible screenshot for depiction on the display of the guidance system, showing the position and orientation of the needle according to one embodiment.

The above position and orientation information determined by the guidance system 10, together with the length of the cannula 102 and position of the magnetic element 110 with respect to the distal needle tip as known by or input into the system, enable the system to accurately determine the location and orientation of the entire length of the needle 100 with respect to the sensor array 90. Optionally, the distance between the magnetic element 110 and the distal needle tip is known by or input into the guidance system 10. This in turn enables the guidance system 10 to superimpose an image of the needle 100 on to an image produced by the ultrasound beam 122 of the ultrasound probe 40. FIGS. 6A and 6B show examples of such a superimposition of the needle onto an ultrasound image. Specifically, FIGS. 6A and 6B each show a screenshot 130 that can be depicted on the display 30 (FIG. 2), for instance. In FIG. 6A, an ultrasound image 132 is shown, including depiction of the skin surface 120, and the vessel 126. The ultrasound image 132 corresponds to an image acquired by the ultrasound beam 122 shown in FIGS. 5A and 5B, for instance.

The screenshot 130 further shows a virtual needle image 134 representing the position and orientation of the needle 100 as determined by the guidance system 10 as described above. Because the system is able to determine the location and orientation of the needle 100 with respect to the sensor array 90, the system is able to accurately determine the position and orientation of the needle 100 with respect to the ultrasound image 132 and superimpose it thereon for depiction as the needle image 134 on the display 30. Coordination of the positioning of the needle image 134 on the ultrasound image 132 is performed by suitable algorithms executed by the processor 22 or other suitable component of the guidance system 10.

The magnetic sensors 92 are configured to continuously detect the magnetic field associated with the magnetic element 110 of the needle 100 during operation of the guidance system 10. In certain embodiments, rather than incorporating the magnetic element 110 with a magnetic field, the needle 100 itself may be magnetized to produce a magnetic field, thus requiring fewer components. Examples of magnetized needles, magnetizing systems, and magnetizers are disclosed in U.S. Patent Publication No. 2018/0310955, which is incorporated herein by reference in its entirety. The process of continuous detection by the sensors enables the guidance system 10 to continuously update the position and orientation of the needle image 134 for depiction on the display 30. Thus, advancement or other movement of the needle 100 is depicted in real-time by the needle image 134 on the display 30. Note that the guidance system 10 is capable of continuously updating both the ultrasound image 132 and the needle image 134 on the display 30 as movements of the ultrasound probe 40 and the needle 100 occur during a placement procedure or other activity.

FIG. 6A further shows that in one embodiment the guidance system 10 can depict a projected path 136 based on the current position and orientation of the needle 100 as depicted by the needle image 134. The projected path 136 assists a clinician in determining whether the current orientation of the needle 100, as depicted by the needle image 134 on the display 30, will result in arriving at the desired internal body portion target, such as the vessel 126 shown here. Again, as the orientation and/or position of the needle image 134 changes, the projected path 136 is correspondingly modified by the guidance system 10. A target 138, indicating the point where the projected path 136 crosses the plane of the ultrasound image 132, can also be depicted on the display 30 by the guidance system 10. As shown in FIG. 6A, in the present example the target 138 is located within the vessel 126 depicted in the ultrasound image 132. Note that the position of the target 138 on the display 30 can also be modified as the needle 100 and/or the ultrasound image 132 are adjusted. The screenshot 130 also includes an area of probability 139, here depicted as a box, which indicates any possible margin of error of the system due to needle length, needle rigidity and flex, field strength of the magnetic element, field strength of the magnetic needle, magnetic interference, possible discrepancy in alignment of the magnetic axis of the magnetic element with the longitudinal axis of the needle, orientation of the sensor array with respect to the ultrasound imaging plane, etc.

FIG. 6B shows that, in one embodiment, the screenshot 130 can be configured such that the ultrasound image 132 and the needle image 134 are oriented so as to be displayed in a three-dimensional aspect. This enables the angle and orientation of the needle 100, as depicted by the needle image 134, to be ascertained and compared with the intended target imaged by the ultrasound image 132. It should be noted that the screenshots 130 are merely examples of possible depictions produced by the guidance system 10 for display; indeed, other visual depictions can be used. Note further that the particular area of the body being imaged is merely an example; the system can be used to ultrasonically image a variety of body portions, and should not be limited to what is explicitly depicted in the accompanying figures. Further, the system as depicted and described herein can be included as a component of a larger system, if desired, or can be configured as a stand-alone device. Also, it is appreciated that, in addition to the visual information provided on the display 30, aural information, such as beeps, tones, etc., can also be employed by the guidance system 10 to assist the clinician during positioning and insertion of the needle into the patient.

In one embodiment, a length of the needle (or other aspect of a medical component) can be determined by measurement by the probe/system of a characteristic of the magnetic element 110 or magnetic needle, such as its field strength. For instance, in one embodiment the magnetic element 110 of the needle 100, or the magnetized needle, can be positioned at a predetermined distance from the ultrasound probe 40 or at a predetermined location with respect to the ultrasound probe 40. With the magnetic element 110 or magnetic needle so positioned, the sensor array of the ultrasound probe 40 can detect and measure the field strength of the associated magnetic element 110. The system can compare the measured field strength with a stored list of possible field strengths corresponding to different known lengths of needles. The system can match the two strengths and determine the needle length. The needle location and subsequent needle insertion can then proceed as described herein. In another embodiment, instead of holding the magnetic element 110 stationary at a predetermined location, the magnetic element 110 or magnetic needle can be moved about the ultrasound probe 40 such that multiple field strength readings are taken by the ultrasound probe 40. Aspects that can be modified so as to impart different field strengths to a set of magnetic elements include size, shape, and composition of the magnetic element, etc.

Further details are given here regarding use of the guidance system 10 in guiding a needle or other medical device in connection with ultrasonic imaging of a targeted internal body portion ("target") of a patient, according to one embodiment. With the needle 100 and the magnetic element thereof positioned a suitable distance (e.g., two or more feet) away from the ultrasound probe 40 including the sensor array 90, the probe is employed to ultrasonically image, for depiction on the display 30 of the guidance system 10, the target within the patient that the needle is intended to intersect via percutaneous insertion. A calibration of the guidance system 10 can then be initiated, in which algorithms are executed by the processor 22 of the console 20 to determine a baseline for any ambient magnetic fields in the vicinity of where the procedure will be performed. As described below, the guidance system 10 can generate status indicators via various feedback systems to notify the clinician that calibration will need to be performed and/or that the calibration is currently in progress. The guidance system 10 can also be informed of the total length of the needle 100, and/or position of the magnetic element with respect to the distal needle tip such as by user input, automatic detection, or in another suitable manner, as has been discussed above.

The needle 100 can then be brought into the range of the magnetic sensors 92 of the sensor array 90 of the ultrasound probe 40. Each of the magnetic sensors 92 detects the magnetic field strength associated with the magnetic element 110 of the needle 100, or with the magnetic needle, which data is forwarded to the processor 22. In one embodiment, such data can be stored in memory until needed by the processor. As the magnetic sensors 92 detect the magnetic field, suitable algorithms are performed by the processor 22 to calculate a magnetic field strength of the magnetic needle, or the magnetic element 110 of the needle 100 at predicted points in space in relationship to the probe. The processor 22 then compares the actual magnetic field strength data detected by the magnetic sensors 92 to the calculated field strength values. Note that this process is further described by the U.S. patents identified above. This process can be iteratively performed until the calculated value for a predicted point matches the measured data. Once this match occurs, the magnetic element 110 has been positionally located in three-dimensional space. Using the magnetic field strength data as detected by the magnetic sensors 92, the pitch and yaw (i.e., orientation) of the magnetic element 110 can also be determined. Together with the known length of the needle 100 and the position of the distal tip of the needle with respect to the magnetic element, this enables an accurate representation of the position and orientation of the needle can be made by the guidance system 10 and depicted as a virtual model, i.e., the needle image 134, on the display 30. Note that the predicted and actual detected values must match within a predetermined tolerance or confidence level in one embodiment for the guidance system 10 to enable needle depiction to occur.

Depiction of the needle image 134 of the needle 100 as described above is performed in the present embodiment by overlaying the needle image on the ultrasound image 132 of the display 30 (FIGS. 6A, 6B). Suitable algorithms of the guidance system 10 as executed by the processor 22 or other suitable component further enable the projected path 136, the target 138, and the area of probability 139 (FIGS. 6A, 6B) to be determined and depicted on the display 30 atop the ultrasound image 132 of the target. The above prediction, detection, comparison, and depiction process is iteratively performed to continue tracking the movement of the needle 100 in real-time.

Clinicians may desire to enhance the ultrasound image by positioning the probe within a proper calibration area by adjusting or fine-tuning the placement of the needle and/or the probe during procedures. In many embodiments, the guidance system 10 can provide sensory feedback to the clinician to facilitate better placement within the calibration area, and thus provide more efficient procedures by reducing the risk of improper movements, or the time needed to complete. The guidance system 10 can facilitate this by providing status indicators to clinicians based on measurements or other data received during the procedure. Such status indicators can, for example, inform the clinician that the needle 100 and/or the ultrasound probe 40 needs to be calibrated, that the ultrasound probe 40 needs to be moved a particular amount about an axis to remain in the calibration zone, or if a communication fault exists in the guidance system 10. Typically, transmitting these status indicators to the clinician during the procedure can require the clinician to break focus on a given task to seek out the current status in another location within the guidance system 10. For example, a clinician focusing on orientating the ultrasound probe 40 along the skin surface 120 of the patient may require the visual attention of the clinician during the process, which can be diverted by having to look on the display 30 to see the current status. Conversely, a clinician looking at the ultrasound area of a display 30 during a procedure may have to divert focus to determine the current status of the system elsewhere on the screen or by observing the positioning of the ultrasound probe 40.

Therefore, it is desired to provide sensory feedback such that the clinician can receive the feedback without substantially changing their focus or area of attention. Thus, by providing status indicators, such as on the ultrasound probe 40, on the display 30, or via wearables or other sounds, the clinician can remain focused on a particular task without needing to look elsewhere.

Figure 7A:
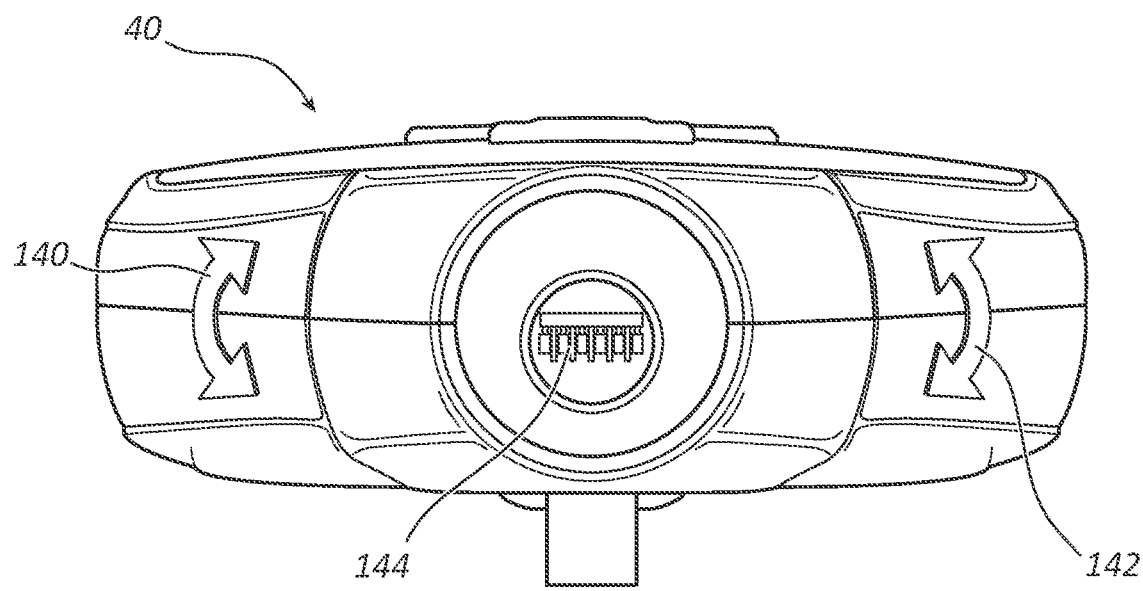
FIG. 7A shows a possible configuration for indicator lights located on the top of a probe of the guidance system, arranged on opposing ends and shaped in bi-directional arrows according to one embodiment.
Figure 7B:
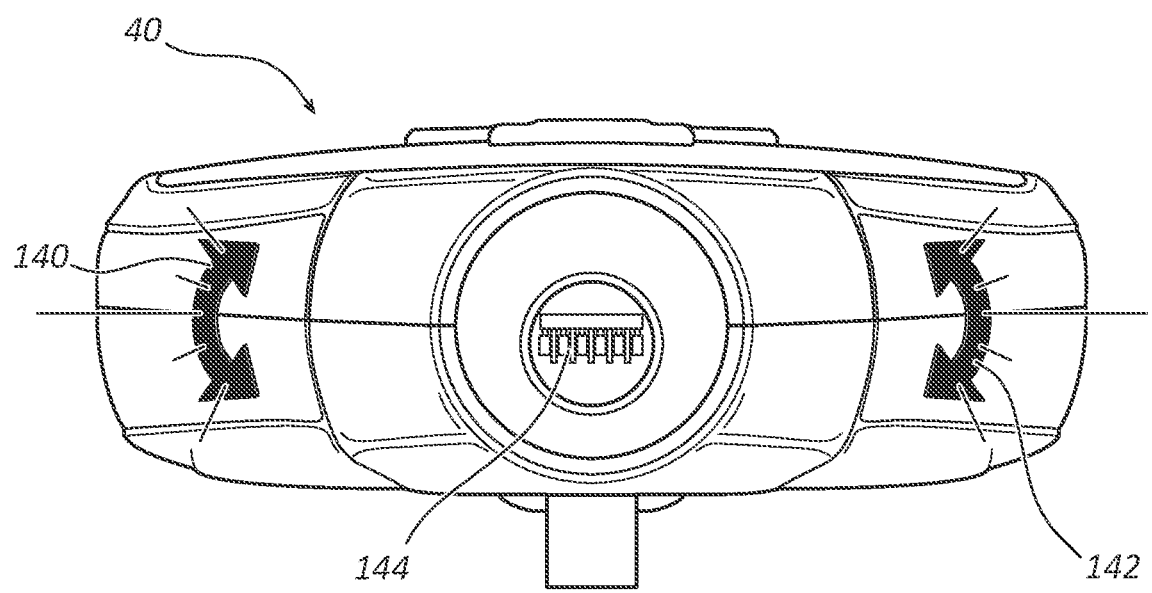
FIG. 7B shows the light-emitting diodes of FIG. 7A in an "on" state.

Reference is now made to FIGS. 7A and 7B in describing one embodiment of providing sensory feedback during the guidance process. The ultrasound probe 40 is shown having two indicator lights located at the top of the probe, specifically a left status indicator light 140 and a right status indicator light 142. The probes depicted in FIGS. 7A-7D are shown in their top view, which would typically be pointed upward and within view of a clinician during the guidance process. The left status indicator light 140 and the right status indicator light 142 are situated on opposing sides of the probe, in between a communication cord inlet 144, which provides the opening by which the communications cord can enter the ultrasound probe 40.

In one embodiment, the left and right status indicator lights 140 and 142 can be configured to change from an "off" state (see FIG. 7A) to an "on" state (see FIG. 7B), optionally in one or more series of patterns. Further, the left and right status indicator lights 140 and 142 can comprise multiple light-emitting diodes (LEDs) within each status indicator light to provide a variety of colors dependent upon the types of LEDs chosen. In certain embodiments, the LEDs may be multi-color and provide color changes programmatically instead of via multiple, single-color LEDs. Typically, the LEDs are situated within the housing of the ultrasound probe 40 under a transparent or semi-transparent window in cut-away in the probe housing. In the embodiment depicted in FIGS. 7A-7C, the cutaway within the probe housing and the window disposed therein comprise a shape that can convey direction information, such as a bi-directional arrow.

The LEDs of the ultrasound probe 40 can be independently operated for state (i.e., off and on) as well as intensity and color. FIG. 7A shows the left and right status indicator lights 140 and 142 in an "off" state, while the left and right status indicator lights 140 and 142 of FIG. 7B are shown in an "on" state. It would be understood by those skilled in the art that a great variety of information can be indicated via the possible combinations of the controllable properties of the LEDs. For example, one or more series of light patterns can convey information such as a status associated with calibration of a component of the guidance system, a suggested direction to move the probe to increase tracking accuracy, or the like. Indeed, the one-or-more series of light patterns can include a plurality of colors to indicate the suggested direction to move the probe to increase tracking accuracy, wherein changing between at least two of the plurality of colors is associated with the suggested direction.

LEDs can indicate to the clinician when the ultrasound probe 40 or the needle 100 needs calibration by, for example, generating a pair of solid yellow lights within the left and right status indicator lights 140 and 142. Similarly, yellow blinking lights can be programmed to communicate to the clinician that the calibration is currently in progress. Other color and intensity combinations can communicate that the ultrasound probe 40 or other component is not properly connected or in proper communication within the guidance system 10 (by showing, for example, a solid red light on both the left and right status indicator lights 140 and 142). The presence of other colors, such as solid green lights, may communicate to the clinician that the tracking is currently in a ready state and can proceed.

By placing the LEDs within a cutaway shape, such as a bi-directional arrow, the changing of LED state, color, and intensity can communicate to the clinician how to adjust the pitch or other orientation of the needle 100 and/or the ultrasound probe 40 during guidance. This can, for example, help keep the ultrasound probe 40 and/or the needle 100 within the calibration zone, and can require less effort by the clinician to acquire status updates as their eyes can be focused on the ultrasound probe 40 and not on the display 30, if desired.

Figure 7C:
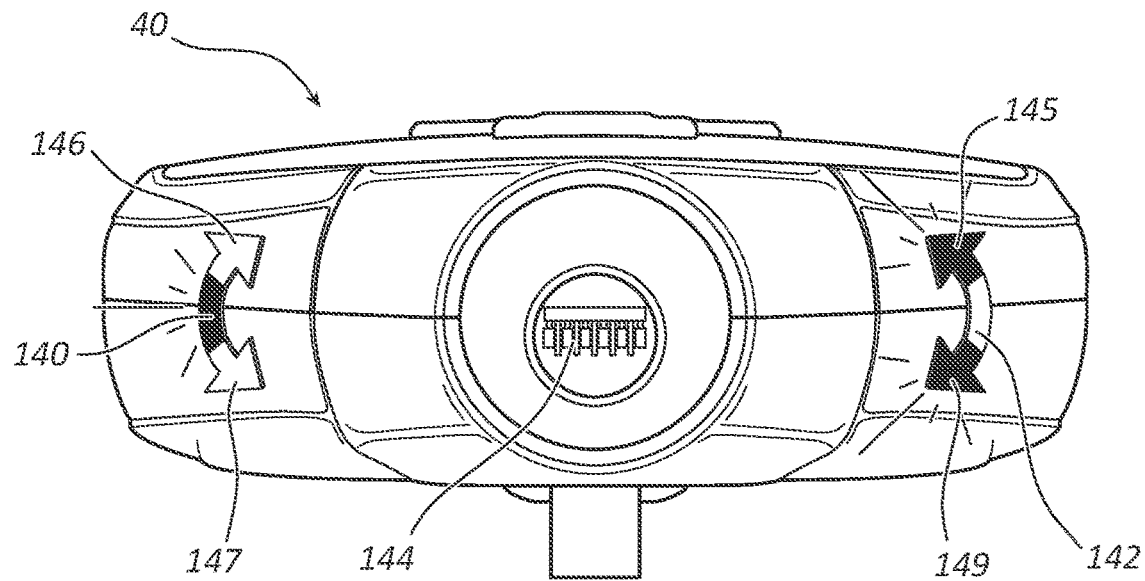
FIG. 7C shows another possible configuration for the light-emitting diodes located on the top of the probe of the guidance system, arranged on opposing ends and shaped in a bi-directional arrow according to one embodiment.

Furthermore, LEDs can be situated at different locations under the cutaway of the probe housing. In this way, increased directional information can be transmitted to the clinician. FIG. 7C shows the ultrasound probe 40 with illuminated LEDs situated in the middle of the left and right status indicator lights 140 and 142. In one embodiment, LEDs are placed within or under the window of the left status indicator light 140 at a center, a forward-facing portion 146, and a rear-facing portion 147 of the window. Similar arrangements can be found on the right status indicator light 142, including forward- and rear-facing portions 145 and 149 of the window in addition to LEDs in a center of the bi-directional arrow cutaway under the window.

By placing LEDs at different points of the bi-directional arrow cutaways on the left and right status indicator lights 140 and 142, the changing of light state, color, and intensity can communicate increased amounts of information regarding the status. For example, by illuminating both ends of the bi-directional arrows in either direction, the clinician can be notified that the pitch of the ultrasound probe 40 should be changed by moving the probe's pitch toward the direction indicated by the LEDs. In other embodiments, by illuminating the LEDs at opposite ends of the bi-directional arrows of the left and right status indicator lights 140 and 142, the guidance system 10 can indicate that the yaw of the ultrasound probe 40 should be adjusted in the indicated direction.

The magnitude of adjustment needed can also be communicated via color changes and/or light intensity. A green LED, for example, lit at the forward-facing portion 146 of the window of the left status indicator light 140 in conjunction with a green LED lit at the rear-facing portion 149 of the right status indicator light 142 can communicate a status that the yaw of the probe should be adjusted in a clockwise direction. By changing the color of the LED from green, to yellow, and then to red can, in one embodiment, indicate a progressively stronger indication to change the yaw of the probe in the indicated direction. Similarly, the LEDs may progressively increase in light intensity in relation to the suggested change in movement of the ultrasound probe 40.

Figure 7D:
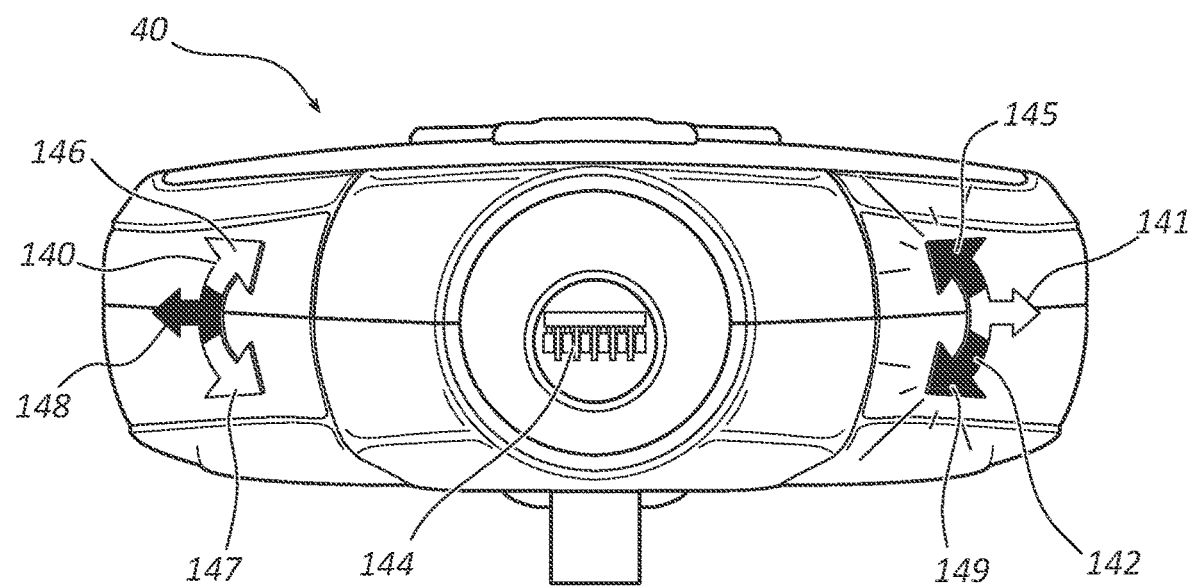
FIG. 7D shows a possible configuration for the light-emitting diodes located on the top of the probe of the guidance system, arranged on opposing ends and shaped in a tri-directional arrow according to one embodiment.

As shown in FIG. 7D, the left and right status indicator lights 140 and 142 can include tri-directional cutaways in the ultrasound probe 40. The left status indicator light 140 is comprised of the forward-facing portion 146 (e.g., an arrow), the rear-facing portion 147 (e.g., an arrow), and a side-facing arrow 148 (e.g., an arrow) of the window and the LED thereunder. Similarly, the right status indicator light 142 also comprises the forward-facing portion 145 (e.g., an arrow), the rear-facing portion 149 (e.g., and arrow), and a side-facing portion 141 (e.g., an arrow) of the window and the LED thereunder. In certain embodiments, the addition of the side-facing portions 141 and 148 can communicate to the clinician a suggested adjustment to move the ultrasound probe 40 to either side. In one embodiment, the side-facing portions 141 and 148 include separate LEDs that can be lit separately from the other LEDs of the left and right status indicator lights 140 and 142. This allows another degree of communication between the guidance system and the clinician by changing the state, color, and/or intensity of the light on either side-facing portion 141 or 148. In this way, the tri-directional left and right status indicator lights 140 and 142 can communicate to the clinician how to orientate the ultrasound probe 40 along three separate axes without the need to look at the display 30.

Reference is now made to FIGS. 8A and 8B, which show another embodiment of an ultrasound probe 840 with a bi-directional status indicator light 150 located on the front side of the ultrasound probe 840. The bi-directional indicator light 150 includes a left-facing portion 152 (e.g., an arrow) and a right-facing portion 154 (e.g., an arrow). The embodiment shown in FIG. 8B has the bi-directional indicator light 150 turned "on" providing a solid light. As discussed above, this type of status indicator can be utilized, for example, to inform the clinician of a calibration status (yellow), an error state (red), or a ready state (green). Similarly, as shown in FIG. 8B, the bi-directional status indicator light 150 can be lit in specific areas to increase the detail and amount of information that can be communicated to the clinician. Methods and means of utilizing distinct areas of a multi-area status indicator light are discussed above in FIGS. 7C and 7D and may be utilized within the ultrasound probe 840 shown in FIG. 8B, as well as any other similar embodiment.

Reference is now made to FIGS. 9A-9D, which show screenshots 930 of status indicator boxes 162 (e.g., colored boxes) on the display 30 during operation of the guidance system 10. As discussed above, the display 30 of the guidance system 10 can show an image produced by the ultrasound beam 122 with a superimposed image of the needle 100 as its location is tracked and determined. While the clinician is looking at the images presented on the display 30, it can be beneficial to communicate issues relating to calibration, ready state, and/or faults in the guidance system 10.

As shown in FIG. 9A, the screenshot 930 of the display 30 includes a status indicator box 162 that surrounds the ultrasound image area. In one embodiment, the status indicator box 162 is a static (e.g., non-blinking) colored (e.g., yellow or a similar high-contrast color) indicator box to inform the clinician that the guidance system 10 requires calibration. The status indicator box 162 is configured to allow the clinician to easily notice and see the status indicator box 162, along with accompanying status indicator text 164, and/or a status indicator icon 166. The status indicator box 162 along with the associated status indicator text 164 and status indicator icon 166 can be designed to be easily sensed by the clinician, even if they are focused on the ultrasound area during a procedure. For example, the status indicator box 162 can be a high-contrast color easily perceptible and recognizable by a clinician via their peripheral awareness without the need to change focus away from the ultrasound or other image on the display 30.

Similarly, the screenshot 930 of FIG. 9B corresponds to a calibration in progress, for example, after the clinician perceived one or more of the status indicators 162, 164, and 166 of FIG. 9A and started a calibration process. Similar to the status indicator box 162 of FIG. 9A, the status indicator box 162 of FIG. 9B can be colored (e.g., yellow or another high-contrast color) suited for being perceived by the clinician. In one embodiment, the method of status indication of the system 10 performing a calibration is to display the status indicator box 162 with a blinking yellow color along with the associated status indicator text 164.

Reference is now made to FIGS. 9C and 9D, which show further screenshots 930 of the display 30 including the status indicator box 162. When the guidance system 10 is in a ready state for use, the status box indicator 162 can be displayed with lower contrast and the associated status indicator text 164. In one embodiment, the guidance system 10 displays the status indicator box 162 in solid green when a ready state has been reached and the clinician can begin or continue the procedure. In other embodiments, the guidance system 10 may remove the status indicator box 162 during the ready state so as to create a larger amount of contrast when a change in status triggers the display of another status indicator box 162 and the associated status indicator text 164. The ultrasound probe 40 or some other component, for example, may lose communication, report some sort of error or fault within the guidance system 10. This can trigger the display of the status indicator box 162 with a high contrast color and the associated status indicator icon 166 as shown in FIG. 9D. In one embodiment, the detected presence of a fault or specific error within the guidance system 10 facilitates the display of the status indicator box 162 around the ultrasound image in solid red optionally with the status indicator icon 166 as an error icon. When the fault or error is fixed, the display 30 can remove or otherwise change the status indicator box 162 and associated status indicator icon 166. In this way, the guidance system 10 is configured to prompt reactions and corrections by the clinician, which can improve the overall efficiency of the procedures performed.

In view of the foregoing, the status indicator box 162 by way of its color (e.g., green, yellow, red, etc.), animation (e.g., blinking, breathing, etc.) or lack thereof, or the like provides patterns (e.g., color patterns) useful for indicating statuses (e.g., calibrating, error, ready, etc.) associated the guidance system 10 or components thereof.

It can be appreciated that other forms of sensory-based feedback can be achieved in order to reduce clinician distractions and increase focus while performing procedures. In some embodiments, the ultrasound probe 40 or guidance system display 30 can emit audible cues that correspond to various statuses of the guidance system 10. The level, pitch, and timbre can be varied based on the different statuses available. These audible status indicator sounds can be pre-programmed or adjusted by the clinician based on preference.

In one embodiment, the ultrasound probe 40 contains at least one vibration-generating component that can provide a noticeable level of haptic feedback. Similar to other status indicators, the vibrations generated in the ultrasound probe 40 can vary depending on the status being indicated. The ultrasound probe 40 can, for example, produce a low-level vibration when the probe is being moved outside of the calibration zone, with the vibration level intensity increasing as the probe is moved further outside of that calibration zone. Similarly, short burst vibrations can be utilized in succession to indicate calibration may be needed and/or that calibration is occurring. It is appreciated that low-level vibrations are typically used so as to avoid the vibrations interfering with the use of the ultrasound probe 40 and the needle 100.

The sensory feedback can also be generated on a clinician's linked wearable device and transmitted to the clinician. In one embodiment, the user may have a pair of smart glasses that can generate images related to status warnings that are visible within the clinician's field of view, allowing the clinician to be aware of the guidance system status no matter what they are looking. Similarly, a smart watch can be connected wirelessly to the guidance system 10 and thus provide status indications via vibrational alerts or triggered audio and/or visual cues on the smart watch. For example, the smart watch may be configured to provide haptic feedback to the clinician similar to the vibrational components residing in the ultrasound probe 40, as discussed above. In other embodiments, the smart watch can be configured to deliver an audible sound similar to the audible status notification sounds also as described above.

Although particular combinations of colors, orientations, directions, and feedback intensities have been discussed in the above figures, it is appreciated that other combinations can be utilized based on the application desired. Similarly, although many embodiments above include LEDs, other light-emitting devices can be utilized to generate similar status indications. Lastly, it is appreciated that the status indicator box 162, the associated status indicator text 164, and the status indicator icons 166 of FIGS. 9A-9D are shown as enclosing the ultrasound image, other embodiments can be utilized that provide alternative arrangements and combinations of similar contrasting images on the display 30 depending on the desired application.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A guidance system for guiding insertion of a needle into a body of a patient, comprising:
   an ultrasound imaging device including a probe for ultrasonically imaging an internal body portion target;
   at least one sensor included with the probe that senses a magnetic field associated with the needle;
   a processor that receives magnetic field data sensed by the at least one sensor to determine a determined position of the needle in three spatial dimensions; and
   a display that depicts the determined position of the needle together with image of the internal body portion target;
   wherein the ultrasound imaging device is configured to provide at least one indication of status via sensory feedback based on the determined position of the needle,
   wherein the sensory feedback is delivered via visible light produced by a plurality of light-emitting diodes located on the probe, the plurality of light-emitting diodes configured to emit a series of light patterns to indicate a suggested direction to move the probe to increase tracking accuracy, and
   wherein the plurality of light-emitting diodes are configured to provide illumination to:
      a first directional indicator disposed on a first side of the probe, the first directional indicator including a first arrow pointing toward a first direction and a second arrow pointing toward a second direction opposite the first direction, and
      a second directional indicator disposed on a second side of the probe opposite the first side, the second directional indicator including a third arrow pointing toward the first direction and a fourth arrow pointing toward the second direction.

2. The guidance system as defined in claim 1, wherein the plurality of light-emitting diodes are configured to emit a second series of light patterns to indicate at least one status associated with calibration of a component of the guidance system.

3. The guidance system as defined in claim 2, wherein the second series of light patterns includes utilizing a plurality of colors to indicate the suggested direction.

4. The guidance system as defined in claim 3, wherein changing between at least two of the plurality of colors is associated with the suggested direction.

5. The guidance system as defined in claim 3, wherein at least two of the plurality of light-emitting diodes are positioned on opposing sides of the probe, and wherein changing between at least two of the plurality of colors of the second series of light patterns is associated with the suggested direction.

6. The guidance system as defined in claim 1, wherein the sensory feedback is delivered via a visual indicator on the display.

7. The guidance system as defined in claim 6, wherein the display is configured to emit a first color pattern to indicate at least one status associated with calibration of a component of the guidance system.

8. The guidance system as defined in claim 6, wherein the display is configured to emit a second color pattern to indicate at least one error within the guidance system.

9. The guidance system as defined in claim 6, wherein the display is configured to emit a third color pattern to indicate a ready state within the guidance system.

10. The guidance system as defined in claim 1, wherein the sensory feedback is delivered via a visual image generated via a wearable device connected to the guidance system.

11. The guidance system as defined in claim 1, wherein the sensory feedback is delivered via tactile feedback generated within the probe.

12. The guidance system as defined in claim 1, wherein the sensory feedback is delivered via an audio signal delivered via a speaker within the guidance system.

13. The guidance system as defined in claim 1, wherein:
a first subset of the plurality of light-emitting diodes is configured to illuminate the first arrow and the third arrow to suggest movement of the probe in accordance with a first axis, and
a second subset of the plurality of light-emitting diodes is configured to illuminate the first arrow and the fourth arrow to suggest movement of the probe in accordance with a second axis perpendicular to the first axis.

14. A method for guiding a needle for insertion into a body of a patient utilizing imaging technology, the method comprising:
(a) imaging a target within the body;
(b) sensing a detectable characteristic relating to the needle via a probe;
(c) determining a determined position of the needle in at least two spatial dimensions by data relating to the detectable characteristic and a sensed extent of bending;
(d) displaying the determined position of the needle with respect to the target together with an image of the target; and
(e) providing at least one indication of status via sensory feedback based on the determined position of the needle,
wherein the sensory feedback is delivered via visible light produced by a plurality of light-emitting diodes located on the probe, the plurality of light-emitting diodes configured to emit a first series of light patterns to indicate a suggested direction to move the probe to increase tracking accuracy,
wherein the plurality of light-emitting diodes are configured to provide illumination to:
a first directional indicator disposed on a first side of the probe, the first directional indicator including a first arrow pointing toward a first direction and a second arrow pointing toward a second direction opposite the first direction, and
a second directional indicator disposed on a second side of the probe opposite the first side, the second directional indicator including a third arrow pointing toward the first direction and a fourth arrow pointing toward the second direction, the method further comprising:
(f) activating a first subset of the plurality of light-emitting diodes to illuminate the first arrow and the third arrow to suggest movement of the probe in accordance with a first axis.

15. The method for guiding as defined in claim 14, wherein the plurality of light-emitting diodes are configured to emit a second series of light patterns to indicate at least one status associated with calibration of a component of a guidance system.

16. The method for guiding as defined in claim 15, wherein the second series of light patterns includes utilizing a plurality of colors to indicate the suggested direction.

17. The method for guiding as defined in claim 16, wherein changing between at least two of the plurality of colors is associated with the suggested direction.

18. The method for guiding as defined in claim 16, wherein at least two of the plurality of light-emitting diodes are positioned on opposing sides of the probe, and wherein changing between at least two of the plurality of colors of the second series of light patterns is associated with the suggested direction.

19. The method for guiding as defined in claim 14, wherein the sensory feedback is delivered via a visual indicator on a display.

20. The method for guiding as defined in claim 19, wherein the displaying further emits a first color pattern to indicate at least one status associated with calibration of at least one component.

21. The method for guiding as defined in claim 19, wherein the displaying further emits a second color pattern to indicate at least one error.

22. The method for guiding as defined in claim 19, wherein the displaying further emits a third color pattern to indicate a ready state.

23. The method for guiding as defined in claim 14, wherein the sensory feedback is delivered via a visual image generated by a wearable device.

24. The method for guiding as defined in claim 14, wherein the sensory feedback is delivered via tactile feedback generated within the probe.

25. The method for guiding as defined in claim 14, wherein the providing sensory feedback further includes delivering an audio signal via a speaker.

26. The method for guiding as defined in claim 14, further comprising:
(g) activating a second subset of the plurality of light-emitting diodes configured to illuminate the first arrow and the fourth arrow to suggest movement of the probe in accordance with a second axis perpendicular to the first axis.

27. The method for guiding as defined in claim 26, wherein:
the first directional indicator further includes a fifth arrow pointing in a third direction perpendicular to the first direction,
the second directional indicator further includes a sixth arrow pointing in a fourth direction opposite the third direction, and the method further comprises:
- (h) activating a third subset of the plurality of light-emitting diodes configured to illuminate one of the fifth arrow or the sixth arrow to suggest movement of the probe in accordance with a third axis perpendicular to the first axis and the second axis.

28. A guidance system for guiding insertion of a needle into a body of a patient, comprising:
- an ultrasound imaging device including a probe for ultrasonically imaging an internal body portion target within a calibration zone determined by a calibration process;
- at least one sensor included with the probe that senses a magnetic field associated with the needle;
- a processor that receives magnetic field data sensed by the at least one sensor to determine a determined position of the needle in three spatial dimensions within the calibration zone; and
- a display that depicts the determined position of the needle together with an image of the internal body portion target;
- wherein the ultrasound imaging device is configured to provide at least one indication of status via sensory feedback from a plurality of light-emitting diodes placed on the probe;
- wherein the sensory feedback includes generating visual notifications that the probe is being moved near a border of the calibration zone;
- wherein the sensory feedback includes producing a low-level vibration in the probe when the probe is moved outside of the calibration zone; and
- wherein the plurality of light-emitting diodes are configured to provide illumination to:
  - a first directional indicator disposed on a first side of the probe, the first directional indicator including a first arrow pointing toward a first direction and a second arrow pointing toward a second direction opposite the first direction, and
  - a second directional indicator disposed on a second side of the probe opposite the first side, the second directional indicator including a third arrow pointing toward the first direction and a fourth arrow pointing toward the second direction.

29. The guidance system as defined in claim 28, wherein:
- the first directional indicator further includes a fifth arrow pointing in a third direction perpendicular to the first direction, and
- the second directional indicator further includes a sixth arrow pointing in a fourth direction opposite the third direction.

30. The guidance system as defined in claim 29, wherein:
- a first subset of the plurality of light-emitting diodes are configured to illuminate the first arrow and the third arrow to suggest movement of the probe in accordance with a first axis, and
- a second subset of the plurality of light-emitting diodes are configured to illuminate the first arrow and the fourth arrow to suggest movement of the probe in accordance with a second axis perpendicular to the first axis.

* * * * *